US006500945B2

(12) United States Patent
Cook

(10) Patent No.: US 6,500,945 B2
(45) Date of Patent: *Dec. 31, 2002

(54) NUCLEOTIDES HAVING CHIRAL PHOSPHORUS LINKAGES

(75) Inventor: Phillip Dan Cook, Carlsbad, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/784,917

(22) Filed: Feb. 16, 2001

(65) Prior Publication Data

US 2001/0008936 A1 Jul. 19, 2001

Related U.S. Application Data

(60) Continuation of application No. 09/208,533, filed on Dec. 9, 1998, now Pat. No. 6,239,265, which is a continuation of application No. 08/635,009, filed on Apr. 19, 1996, now Pat. No. 5,852,188, which is a division of application No. 08/058,023, filed on May 5, 1993, now Pat. No. 5,521,302, which is a division of application No. 07/777,670, filed on Oct. 15, 1991, now Pat. No. 5,212,295.

(51) Int. Cl.[7] .............................................. C07H 19/00

(52) U.S. Cl. .................. 536/26.7; 536/25.33; 536/26.8

(58) Field of Search ...................... 536/26.7, 26.8, 536/25.33

(56) References Cited

U.S. PATENT DOCUMENTS

| 5,212,295 | A | | 5/1993 | Cook | 536/26.7 |
|---|---|---|---|---|---|
| 5,506,212 | A | | 4/1996 | Cook et al. | 514/44 |
| 5,512,668 | A | | 4/1996 | Stec et al. | 536/25.33 |
| 5,521,302 | A | | 5/1996 | Cook | 514/44 |
| 5,576,302 | A | | 11/1996 | Cook et al. | 536/25.4 |
| 5,599,797 | A | | 2/1997 | Cook et al. | 536/25.33 |
| 5,607,923 | A | | 3/1997 | Cook et al. | 536/25.34 |
| 5,620,963 | A | | 4/1997 | Cook et al. | 536/24.5 |
| 5,635,488 | A | | 6/1997 | Cook et al. | 514/44 |
| 5,646,267 | A | | 7/1997 | Stec et al. | 536/25.33 |
| 5,852,188 | A | * | 12/1998 | Cook | |
| 5,856,465 | A | | 1/1999 | Stec et al. | 536/25.3 |
| 5,883,237 | A | | 3/1999 | Stec et al. | 536/23.1 |
| 6,239,265 | B1 | * | 5/2001 | Cook | |

FOREIGN PATENT DOCUMENTS

| EP | 0 506 242 A1 | 9/1992 |
|---|---|---|
| WO | WO 96/37503 | 11/1996 |
| WO | WO 97/09340 | 3/1997 |

OTHER PUBLICATIONS

Brody, R. et al., "Stereochemical coruse of nucleotidyl catalyzed by bacteriphage T7 induced DNA polymerase", Biochemistry 1982, 21, 2570–2572.

Brody, R. and Frey, P., "Unambiguous determination of the sterochemistry of nucleotidyl transfer catalyzed by DNA polymerase I from *escherichia coli*", Biochemistry 1981, 20, 1245–1252.

Bryant, F. and Benkovic, S., "Stereochemical course of the reaction catalyzed by 5'–nucleotide phosphodiesterase from snake venom", Biochemistry 1979, 2825–2628.

Burgers, P. and Eckstein, F., "Absolute configuration of the diastereomers of adenosine 5'–O–(1–thiotriphosphate): Consequences for the stereochemistry of polymerization by DNA–dependent RNA polymerase from *Escherichia coli*", Proc. Natl. Acad. Sci. USA 1978, 75(10), 4798–4800.

Burgers, P. and Eckstein, F., "A study of the mechanism of DNA polymerase I from *escherichia coli* with diastereomeric phosphorothioate analogs of deoxyadenosine triphosphate", J. of Biological Chemistry 1979, 254(15), 6889–6893.

Cruse et al., "Chiral Phosphorothioate Analogues of B–DNA", J.Mol.Biol. 1986, 192, 891–905.

Ecksten, F., "Nucleotide Phosphorothioates", Journal of the American Chemical Society 1970, 92, 4718–4723.

Eckstein, F and Jovin, T.M., "Assignment of Resonances in the Phosphorus–31 Nuclear Magnetic Resonance Spectrum of Poly[d(A–T)] from phosphorothioate Substitution", Biochemistry 1983, 22, 4546–4550.

Fujii, et al., "Acylphosphonates. 7.[1] A New Method for Sterospecific and Steroselective Generation of Dideoxyribonucleoside Phosphorothiates via the Acylphosphonate Intermediates", Tetrahedron 1987, 43, 3395–3407.

Goodchild, J., "Conjugates of Oligonucleotides and Modified Oligonucleotides: A Review of Their Synthesis and Properties", Bioconjuage Chemistry 1990, 1, 165–187.

Gupta, et al., "Template–Primer–Dependent Turnover of (Sp)–dATP S by T4 DNA Polymerase", The Journal of Biological Chemistry 1982, 257, 7689–7692.

Haga, K. et al., "The preparation of halo–nucleosides", Bull. of the Chem. Soc. Jpn. 1970, 43, 3922–3924.

Holy, A., "Nucleic acid components and their analogues. IC. synthesis of 6–azauridine 5'–methanephosphonate and 6–azauridine 2'(3')–methanephosphonate", Collection Czechoslov. Chem. Commun. 1967, 32, 3713–3718.

(List continued on next page.)

Primary Examiner—James O. Wilson
(74) Attorney, Agent, or Firm—Woodcock Washburn LLP

(57) ABSTRACT

Sequence-specific oligonucleotides are provided having substantially pure chiral Sp phosphorothioate, chiral Rp phosphorothioate, chiral Sp alkylphosphonate, chiral Rp alkylphosphonate, chiral Sp phosphoamidate, chiral Rp phosphoamidate, chiral Sp phosphotriester, and chiral Rp phosphotriester linkages. The novel oligonucleotides are prepared via a stereospecific $SN_2$ nucleophilic attack of a phosphodiester, phosphorothioate, phosphoramidate, phosphotriester or alkylphosphonate anion on the 3' position of a xylonucleotide. The reaction proceeds via inversion at the 3' position of the xylo reactant species, resulting in the incorporation of phosphodiester, phosphorothioate, phosphoramidate, phosphotriester or alkylphosphonate linked ribofuranosyl sugar moieties into the oligonucleotide.

9 Claims, No Drawings

OTHER PUBLICATIONS

Holy, A. and Sorm, F., "Oligonucleotidic compounds. XXXII. Phosphorylation of 1–lyxofuranosyl, 1–xylofuranosyl and 1–arabinofuranosyl derivatives of uracil and thymine with triethyl phosphite and hexachloracetone", *Collection Czechoslov. Chem. Commun.* 1969, 34, 1929–1953.

Hubert–Habart, M. and Goodman, L., "The direct formation of a 3',5'–cyclic mononucleotide from and adenine nucleoside", *Chemical Communications* 1969, 740–741.

Ikehara, M., "Studies of Nuclosides and Nucleotides–XLI[1]", *Tetrahedron* 1970, 26, 4251–4259.

Jäger, A. et al., "Oligonucleotide N–alkylphosphoramidates: Synthesis and binding to polynucletides", *Biochemistry* 1988, 27, 7237–7246.

Kondo, K. et al., "Studies on biologically active nucleosides and nucleotides.3. synthesis of 9–(3–bromo–3–deoxy–2, 5–di–O–acetyl–B–D–xylofuranosyl) adenine", *J. Org. Chem.* 1977, 42(24), 3957–3958.

Koole, L.H. et al., "Enhanced stability of a Watson & Crick DNA duplex structure by methylation of the phosphate groups in one strand", *Proc. K. Ned. Acad. Wet.* 1987, 90(1), 41–46.

Lee, W.W. et al., "Xylo– and Arabinofuranosylthioguanine and Related Nucleosides Derived from 2–Acetamido–6–chloropurine", *J.Medicin.Chem.* 1971, 14, 819–823.

Letsinger et al., "Effects of pendant groups at phosphorus on binding properties of d–ApA analogues", *Nucleic Acids Research* 1986, 14, 3487–3499.

Letters et al., "$O^2$,3'–Cyclouridine", *J. Chem. Soc..* 1960, 1410–1413.

Lichtenthaler, F.W. et al., *Chem. Ber.* 1969, 102, 964.

Marumoto, R. et al.,"One–step Halogenation at the 2'–Position of Uridine, and Related Reactions of Cytidine and $N^4$–Acetylcytidine", *Chem.Pharm.Bull.* 1974, 22, 128–134.

Miller, N. et al., "Nucleosides. XXI. Synthesis of Some 3'–Substituted 2',3'–Dideoxyribonucleosides of Thymine and 5–Methylcytosine", *J. Org. Chem.* 1964, 29, 1772–1776.

Miller, P.S. et al., "Biochemical and Biological Effects of Nonionic Nucleic Acid Methylphosphonates", *Biochemistry* 1981, 20, 1874–1880.

Mizuno, Y. et al., "A Novel Synthesis of Purine β–D–Nucleosides via Purine 8,5'–S–Anhydronucleosides", *J.Am.Chem.Soc.* 1972, 94, 4737–4739.

Mizuno, Y. et al., "Syntheses of Potential Antimetabolites. XV. Syntheses of Sulfonate Analog of Adenosine 5'–Phosphate and an Alternative Synthesis of 5',8–S–Anhydroadenine Nucleosides and 5'–Deoxyspongoadenosine and Its Isomers", *J.Org.Chem.* 1974, 39, 1440–1444.

Murray, A.W. et al., "Adenosine 5'–Phosphorothioate. A Nucleotide Analog That Is Substrate, Competitive Inhibitor, or Regulator of Some Enzymes That Interact with Adenosine 5'–Phosphate", *Biochemistry* 1968, 4023–4029.

Niewiarowski, W., et al., "Diastereomers of Thymidine 3'0–(Methanephosphono–thioate): Synthesis, Absolute Configuration and Reaction with 3'–methoxyacetylthymidine Under Conditions of Triester Approach to Oligonucleotide Synthesis", *Acta Biochimica Polonia* 1987, 34, 217–231.

Reese, "The Chemical Synthesis of Oligo– and Poly–Nucleotides by the Phosphotriester Approach", *Tetrahedron* 1978, 34, 3143–3179.

Reist et al., "Synthesis of 9–(5–Deoxy–B–D–arabinofuranosyl) adenine", *J. Org. Chem.* 1965, 30, 3401–3403.

Robins et al., "Nucleic acid related compounds. 11. adenosine 2', 3'–ribo–epoxide. synthesis, intramolecular degradation, and transformation into 3'–sustituted xylofuranosyl nucleosides and the lyxo–epoxide[1,2]" *J. Org. Chem.* 1974, 39(11), 1564–1570.

Romaniuk, P. J. and Eckstein, F., "A study of the mechanism of t4 DNA polymerase with diasteromeric phosphorothioate analogues of deoxyadenosine triphosphate", *Biological Chemistry* 1982, 257(13), 7684–7688.

Scheit, K.H. et al., "Nucleotides with Modified Phosphate Groups", *Nucleotide Analogs,* 1980, John Wiley & Sons, Chap. 4, pp. 96–141.

Schuman, D. et al. *J. Am. Chem. Soc.* 1970, 92, 3434.

Stec, W.J., "Stereospecific synthesis of oligonucleotide p–chiral analogues", *Polish Academy of Sciences* 1989, Jun. (18–21).

Stec et al., "Reversed–phase High–performance Liquid Chromatographic Separation of Diastereomeric Phosphorothiate Analogues of Oligodeoxyribonucleotides and Other Backbone–Modified Congeners of DNA", *J. Chromatography* 1985, 326, 263–280.

Suzaki et al., "Synthesis of 9–β–D–Xylofuranosyl–6–mercaptopurine and 9–β–D–Xylofuranosylguanine 5'–Phosphate", *Chem.Pharm.Bull.* 1970, 18, 172–176.

Szarek et al., "Synthesis of 5–Deoxy–D–xylo–Hexose and 5–Deoxy–L–arabino–Hexose, and Their Conversion into Adenine Nucleosides", *Carbohydrate Research* 1978, 62, 89–103.

Uhlmann, E. and Peyman, A., "Antisense oligonucleotides: A new therapeutic principle", *Chemical Reviews* 1990, 90(4), 534–584.

Ueda, T. et al., "Phosphorothioate–containing RNAs show mRNA activity in the prokaryotic translation systems in vitro", *Nucleic Acids Research* 1991, 19, 547–552.

Vince, R. and Daluge, "Synthesis and Antimicrobial Activity of a Carbocyclic Puromycin Analog.6–Dimethylaino–9–1R–[2Rhydroxy–3R–(p–methoxyphenyl–L–alanylamino)]–cyclopentyl)purine", *J. Of Medicinal Chem.* 1971, 15, 171–177.

Wempen, I. And Fox, *J. Org. Chem.* 1969, 34, 1020.

Wiberg, "Physical Organic Chemistry", John Wiley & Sons, 1964, p. 424.

\* cited by examiner

NUCLEOTIDES HAVING CHIRAL PHOSPHORUS LINKAGES

CROSS-REFERENCE TO RELATED APPLICATIONS

This application is a continuation of U.S. application Ser. No. 09/208,533, filed Dec. 9, 1998, now U.S. Pat. No. 6,239,265, which is a continuation of U.S. application Ser. No. 08/635,009, filed Apr. 19, 1996, now U.S. Pat. No. 5,852,188, which is a division of U.S. application Ser. No. 08/058,023, filed May 5, 1993, now U.S. Pat. No. 5,521,302, which is a division of U.S. application Ser. No. 07/777,670, filed Oct. 15, 1991, now U.S. Pat. No. 5,212,295.

FIELD OF THE INVENTION

This invention is directed to sequence-specific oligonucleotides having chiral phosphorus linkages and to a novel chemical synthesis of these and other oligonucleotides. The invention includes chiral alkylphosphonate, chiral phosphotriester, and chiral phosphoramidate-linked oligonucleotides. The invention further includes chiral phosphorothioate, chiral alkylphosphonate, chiral phosphotriester, and chiral phosphoramidate-linked oligonucleotides that contain at least one modified nucleoside unit. The novel chemical synthesis provides such chiral phosphorothioate, chiral alkylphosphonate, chiral phosphotriester, and chiral phosphoramidate oligonucleotides as well as "natural" or "wild type" phosphodiester oligonucleotides.

BACKGROUND OF THE INVENTION

Messenger RNA (mRNA) directs protein synthesis. As a therapeutic strategy, antisense therapy strives to disrupt the synthesis of target proteins by using a sequence-specific oligonucleotide to form a stable heteroduplex with its corresponding mRNA. Such antisense oligonucleotides generally have been natural phosphodiester oligonucleotides.

As contrasted to natural phosphodiester oligonucleotides, the use of phosphorothioate, methylphosphonate, phosphotriester or phosphoramidate oligonucleotides in antisense therapy provides certain distinguishing features. Each of the phosphorothioate, methylphosphonate, phosphotriester or phosphoramidate phosphorus linkages can exist as diastereomers. Certain of these phosphorothioate, methylphosphonate, phosphotriester or phosphoramidate oligonucleotides have a greater resistance to nucleases. Some have solubilities similar to the solubility of natural phosphodiester oligonucleotides. Other have solubilities different from that of the natural phosphodiester oligonucleotides. Some are generally more chemically or thermodynamically stable than the natural phosphodiester oligonucleotides. At least the phosphorothioates have oligonucleotide-RNA heteroduplexes that can serve as substrates for endogenous RNase H.

The phosphorothioate oligonucleotides, like the natural phosphodiester oligonucleotides, are soluble in aqueous media. In contrast, methylphosphonate, phosphotriester, and phosphoramidate oligonucleotides, which lack a charge on the phosphorus group, can penetrate cell membranes to a greater extent and, thus, facilitate cellular uptake. The internucleotide linkage in methylphosphonate oligonucleotides is more base-labile than that of the natural phosphodiester internucleotide linkage, while the internucleotide linkage of the phosphorothioate oligonucleotides is more stable than the natural phosphodiester oligonucleotide linkage.

The resistance of phosphorothioate oligonucleotides to nucleases has been demonstrated by their long half-life in the presence of various nucleases relative to natural phosphodiester oligonucleotides. This resistance to nucleolytic degradation in vitro also applies to in vivo degradation by endogenous nucleases. This in vivo stability has been attributed to the inability of 3'-5' plasma exonucleases to degrade such oligonucleotides. Phosphotriester and methylphosphonate oligonucleotides also are resistant to nuclease degradation, while phosphoramidate oligonucleotides show some sequence dependency.

Since they exist as diastereomers, phosphorothioate, methylphosphonate, phosphotriester or phosphoramidate oligonucleotides synthesized using known, automated techniques result in racemic mixtures of Rp and Sp diastereomers at the individual phosphorothioate, methylphosphonate, phosphotriester or phosphoramidate linkages. Thus, a 15-mer oligonucleotide containing 14 asymmetric linkages has $2^{14}$, i.e. 16,384, possible stereoisomers. Accordingly, it is possible that only a small percentage of the oligonucleotides in a racemic mixture will hybridize to a target mRNA or DNA with sufficient affinity to prove useful in antisense or probe technology.

Miller, P. S., McParland, K. B., Jayaraman, K., and Ts'o, P. O. P (1981), *Biochemistry*, 20:1874, found that small di-, tri- and tetramethylphosphonate and phosphotriester oligonucleotides hybridize to unmodified strands with greater affinity than natural phosphodiester oligonucleotides. Similar increased hybridization was noted for small phosphotriester and phosphoramidate oligonucleotides; Koole, L. H., van Genderen, M. H. P., Reiners, R. G., and Buck, H. M. (1987), *Proc. K. Ned. Adad. Wet.*, 90:41; Letsinger, R. L., Bach, S. A., and Eadie, J. S. (1986), *Nucleic Acids Res.*, 14:3487; and Jager, A., Levy, M. J., and Hecht, S. M. (1988), *Biochemistry*, 27:7237. The effects of the racemic diastereomers on hybridization becomes even more complex as chain length increases.

Bryant, F. R. and Benkovic, S. J. (1979), *Biochemistry*, 18:2825 studied the effects of diesterase on the diastereomers of ATP. Published patent application PCT/US88/03634 discloses dimers and trimers of 2'–5'-linked diastereomeric adenosine units. Niewiarowski, W., Lesnikowski, Z. J., Wilk, A., Guga, P., Okruszek, A., Uznanski, B., and Stec, W. (1987), *Acta Biochimica Polonia*, 34:217, synthesized diastereomeric dimers of thymidine, as did Fujii, M., Ozaki, K., Sekine, M., and Hata, T. (1987), *Tetrahedron*, 43:3395.

Stec, W. J., Zon, G., and Uznanski, B. (1985), *J. Chromatography*, 326:263, have reported the synthesis of certain racemic mixtures of phosphorothioate or methyphosphonate oligonucleotides. However, they were only able to resolve the diastereomers of certain small oligomers having one or two diastereomeric phosphorus linkages.

In a preliminary report, J. W. Stec, Oligonucleotides as antisense inhibitors of gene expression: Therapeutic implications, meeting abstracts, Jun. 18–21, 1989, noted that a non-sequence-specific thymidine homopolymer octomer—i.e. a $(dT)_8$-mer, having "all-except-one" Rp configuration methylphosphonate linkages—formed a thermodynamically more stable hybrid with a 15-mer deoxyadenosine homopolymer—i.e. a $d(A)_{15}$-mer—than did a similar thymidine homopolymer having "all-except-one" Sp configuration methylphosphonate linkages. The hybrid between the "all-except-one" Rp $(dT)_8$-mer and the $d(A)_{15}$-mer had a Tm of 38° C. while the Tm of the "all-except-one" Sp $(dT)_8$-mer and the $d(A)_{15}$-mer was <0° C. The hybrid between a $(dT)_8$-mer having natural phosphodiester linkages, i.e. octathymidylic acid, and the $d(A)_{15}$-mer was reported to have a Tm of 14° C. The "all-except-one" thymidine homopolymer octamers were formed from two thymidine methylphosphonate tetrameric diastereomers linked by a natural phosphodiester linkage.

To date, it has not been possible to chemically synthesize an oligonucleotide having more than two adjacent, chirally pure phosphorous linkages. Indeed, even in homopolymers it has been possible to produce only three such adjacent chiral linkages. For an oligonucleotide to be useful as an antisense compound, many nucleotides must be present. While not wishing to be bound by any particular theory, it is presently believed that generally at least about 10 or more nucleotides are necessary for an oligonucleotide to be of optimal use as an antisense compound. Because it has not been possible to resolve more than two or three adjacent phosphorus linkages, the effects of induced chirality in the phosphorus linkages of chemically synthesized antisense oligonucleotides has not been well assessed heretofore.

Except as noted above, the sequence-specific phosphorothioate, methylphosphonate, phosphotriester or phosphoramidate oligonucleotides obtained utilizing known automated synthetic techniques have been racemic mixtures. Indeed, it was recently stated in a review article that: "It is not yet possible to synthesize by chemical means diastereomerically pure chains of the length necessary for antisense inhibition," see J. Goodchild (1990) *Bioconjugate Chemistry*, 1:165.

The use of enzymatic methods to synthesize oligonucleotides having chiral phosphorous linkages has also been investigated. Burgers, P. M. J. and Eckstein, F. (1979), *J. Biological Chemistry*, 254:6889; and Gupta, A., DeBrosse, C., and Benkovic, S. J. (1982) *J. Bio. Chem.*, 256:7689 enzymatically synthesized diastereomeric polydeoxyadenylic acid having phosphorothioate linkages. Brody, R. S. and Frey, P. S. (1981), *Biochemistry*, 20:1245; Eckstein, F. and Jovin, T. M. (1983), *Biochemistry*, 2:4546; Brody, R. S., Adler, S., Modrich, P., Stec, W. J., Leznikowski, Z. J., and Frey, P. A. (1982) *Biochemistry*, 21: 2570–2572; and Romaniuk, P. J. and Eckstein, F. (1982) *J. Biol. Chem.*, 257:7684–7688 all enzymatically synthesized poly TpA and poly ApT phosphorothioates while Burgers, P. M. J. and Eckstein, F. (1978) *Proc. Natl. Acad. Sci. USA*, 75: 4798–4800 enzymatically synthesized poly UpA phosphorothioates. Cruse, W. B. T., Salisbury, T., Brown, T., Cosstick, R. Eckstein, F., and Kennard, O. (1986), *J. Mol. Biol.*, 192:891, linked three diastereomeric Rp GpC phosphorothioate dimers via natural phosphodiester bonds into a hexamer. Most recently Ueda, T., Tohda, H., Chikazuni, N., Eckstein, R., and Watanabe, K. (1991) *Nucleic Acids Research*, 19:547, enzymatically synthesized RNA's having from several hundred to ten thousand nucleotides incorporating Rp diastereomeric phosphorothioate linkages. Enzymatic synthesis, however, depends on the availability of suitable polymerases that may or may not be available, especially for modified nucleoside precursors.

Thus, while phosphorothioate, alkylphosphonate, phosphoamidate, and phosphotriester oligonucleotides have useful characteristics, little is known concerning the effects of differing chirality at the phosphorus linkages. It would therefore be of great advantage to provide oligonucleotides having phosphorous linkages of controlled stereochemistry.

OBJECTS OF THE INVENTION

Accordingly, it is one object of this invention to provide sequence-specific oligonucleotides having chirally pure phosphorothioate, alkylphosphonate, phosphotriester or phosphoramidate linkages.

It is a further object to provide phosphorothioate, alkylphosphonate, phosphoramidate, and phosphotriester oligonucleotides comprising substantially all Rp or all Sp linkages.

It is another object to provide phosphorothioate, alkylphosphonate, phosphoramidate, and phosphotriester oligonucleotides that have antisense hybridizability against DNA and RNA sequences.

It is still another object of this invention to provide phosphorothioate, alkylphosphonate, phosphoramidate, and phosphotriester oligonucleotides for use in antisense diagnostics and therapeutics.

A further object is to provide research and diagnostic methods and materials for assaying bodily states in animals, especially diseased states.

Another object is to provide therapeutic and research methods and materials for the treatment of diseases through modulation of the activity of DNA and RNA.

It is yet another object to provide new methods for synthesizing sequence-specific oligonucleotides having chirally pure phosphorothioate, methylphosphonate, phosphotriester or phosphoramidate linkages.

SUMMARY OF THE INVENTION

The present invention provides stereoselective methods for preparing sequence-specific oligonucleotides having chiral phosphorous linkages. In certain preferred embodiments, these methods comprise the steps of:

(a) selecting a first synthon having structure (1):

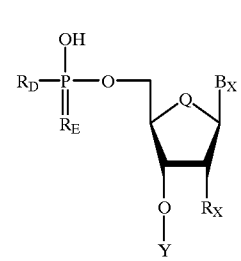

(1)

wherein:

Q is O or $CH_2$;

$R_A$ and $R_B$ are H, lower alkyl, substituted lower alkyl, an RNA cleaving moiety, a group which improves the pharmacokinetic properties of an oligonucleotide, or a group which improves the pharmacodynamic properties of an oligonucleotide;

$R_D$ is O, S, methyl, alkoxy, thioalkoxy, amino or substituted amino;

$R_E$ is O or S;

$R_X$ is H, OH, or a sugar derivatizing group;

$B_X$ is a naturally occurring or synthetic nucleoside base or blocked nucleoside base; and Y is a stable blocking group, a solid state support, a nucleotide on a solid state support, or an oligonucleotide on a solid state support;

(b) selecting a second synthon having structure (2):

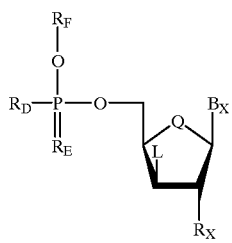
(2)

wherein:
$R_F$ is a labile blocking group; and
L is a leaving group or together L and Bx are a 2-3' or 6-3' pyrimidine or 8-3' purine cyclonucleoside;
(c) adding the second synthon to the first synthon in the presence of a base to effect nucleophilic attack of the 5'-phosphate of the first synthon at the 3'-position of the second synthon to yield a new first synthon having structure (3):

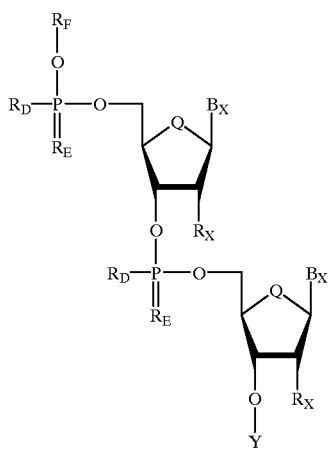
(3)

via a stereospecific inversion of configuration at the 3' position of the second synthon; and
(d) treating the new first synthon with a reagent to remove the labile blocking group RF.

Additional nucleotides are added to the new first synthon by repeating steps (b), (c), and (d) for each additional nucleotide. Preferably, $R_F$ is an acid-labile blocking group and said new first synthon in step (d) is treated with an acidic reagent to remove said acid-labile RF blocking group.

The present invention also provides sequence-specific oligonucleotides comprising a plurality of nucleotides linked by chiral phosphorothioate, methylphosphonate, phosphotriester or phosphoramidate oligonucleotides linkages wherein at least one of the nucleosides is a non-naturally occurring nucleoside. Preferably, the nucleosides are connected via linkages selected from the group consisting of chiral Sp phosphorothioate, chiral Rp phosphorothioate, chiral Sp alkylphosphonate, chiral Rp alkylphosphonate, chiral Sp phosphoamidate, chiral Rp phosphoamidate, chiral Sp chiral phosphotriester or chiral Rp phosphotriester linkages. In one embodiment of the invention each of the linkages of the oligonucleotide is a substantially pure chiral phosphorous linkage. In other embodiments less than all of the phosphate linkages are substantially pure chiral phosphorous linkages. In further embodiments, the oligonucleotides of the invention form at least a portion of a targeted RNA or DNA sequence.

The present invention also provides oligonucleotides comprising nucleoside units joined together by either all Sp phosphotriester linkages, all Rp phosphotriester linkages, all Sp phosphoramidate linkages, or all Rp phosphoramidate linkages. Also provided are oligonucleotides having at least 10 nucleoside units joined together by either all Sp alkylphosphonate linkages or all Rp alkylphosphonate linkages. Preferably such alkylphosphonate linkages are methylphosphonate linkages. Each of these oligonucleotides can form at least a portion of a targeted RNA or DNA sequence.

In preferred embodiments of the invention, the oligonucleotides include non-naturally occurring nucleoside units incorporated into the oligonucleotide chain. Such nucleoside units preferably have structure (4) or structure (5):

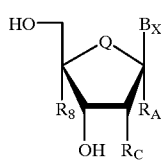
(4)

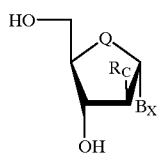
(5)

wherein Q, $R_B$, $R_G$, and $B_X$ are defined as above and $R_C$ is H, OH, lower alkyl, substituted lower alkyl, F, Cl, Br, CN, $CF_3$, $OCF_3$, OCN, O-alkyl, substituted O-alkyl, S-alkyl, substituted S-alkyl, SOMe, $SO_2Me$, $ONO_2$, $NO_2$, $N_3$, $NH_2$, NH-alkyl, substituted NH-alkyl, $OCH_2CH=CH_2$, $OCH=CH_2$, $OCH_2CCH$, OCCH, aralkyl, heteroaralkyl, heterocycloalkyl, poly-alkylamino, substituted silyl, an RNA cleaving moiety, a group which improves the pharmacodynamic properties of an oligonucleotide, or a group which improves the pharmacokinetic properties of an oligonucleotide.

In preferred embodiments, $B_X$ is a pyrimidinyl-1 or purinyl-9 moiety such as, for example, adenine, guanine, hypoxanthine, uracil, thymine, cytosine, 2-aminoadenine or 5-methylcytosine.

In further preferred embodiments, the modified nucleosides include nucleosides having structures (6)–(11):

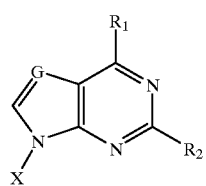
(6)

-continued

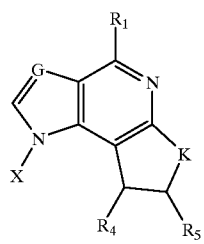
(7)

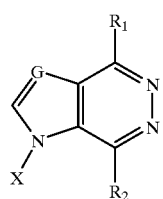
(8)

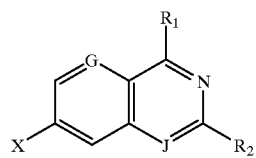
(9)

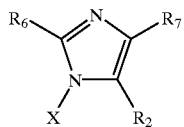
(10)

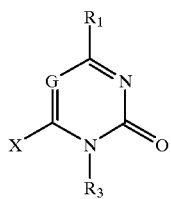
(11)

wherein:

G and K are, independently, C or N;

J is N or $CR_2R_3$;

$R_1$ is OH or $NH_2$;

$R_2$ and $R_3$ are H, NH, lower alkyl, substituted lower alkyl, lower alkenyl, aralkyl, alkylamino, aralkylamino, substituted alkylamino, heterocycloalkyl, heterocycloalkylamino, aminoalkylamino, hetrocycloalkylamino, polyalkylamino, an RNA cleaving moiety, a group which improves the pharmacokinetic properties of an oligonucleotide, or a group which improves the pharmacodynamic properties of an oligonucleotide;

$R_4$ and $R_5$ are, independently, H, OH, $NH_2$, lower alkyl, substituted lower alkyl, substituted amino, an RNA cleaving moiety, a group which improves the pharmacokinetic properties of an oligonucleotide, or a group which improves the pharmacodynamic properties of an oligonucleotide;

$R_6$ and $R_7$ are, independently, H, OH, $NH_2$, SH, halogen, $CONH_2$, $C(NH)NH_2$, $C(O)O$-alkyl, $CSNH_2$, CN, $C(NH)NHOH$, lower alkyl, substituted lower alkyl, substituted amino, an RNA cleaving moiety, a group which improves the pharmacokinetic properties of an oligonucleotide, or a group which improves the pharmacodynamic properties of an oligonucleotide; and X is a sugar or a sugar analog moiety where said sugar analog moiety is a sugar substituted with at least one substituent comprising an RNA cleaving moiety, a group which improves the pharmacodynamic properties of an oligonucleotide, or a group which improves the pharmacokinetic properties of an oligonucleotide.

The present invention also provides compounds which are useful in forming the oligonucleotides of invention. Such compounds have structure (12):

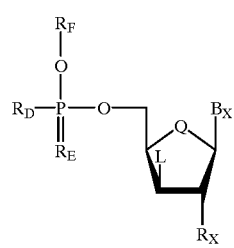
(12)

wherein Q, $R_A$, $R_D$, $R_E$, $R_X$, L, and $B_X$ are defined as above and $R_F$ is H or a labile blocking group.

The oligonucleotides of the invention are useful to increase the thermodynamic stability of heteroduplexes with target RNA and DNA. Certain of the oligonucleotides of the invention are useful to elicit RNase H activity as a termination event. Certain other oligonucleotides are useful to increase nuclease resistance. The oligonucleotides of the invention are also useful to test for antisense activity using reporter genes in suitable assays and to test antisense activity against selected cellular target mRNA's in cultured cells.

DETAILED DESCRIPTION OF THE INVENTION

As will be recognized, adjacent nucleosides of a naturally occurring or wild type oligonucleotide are joined together by phosphodiester linkages, i.e. diesters of phosphoric acid. The natural phosphodiester linkages in oligonucleotides are at the same time both non-chiral and pro-chiral sites. Substitution of one of the oxygen atoms of the phosphate moiety of a nucleotide with another atom yields an asymmetric center on the phosphorus atom. Since a nucleotide unit already contains a first asymmetrical center within its sugar moiety, further asymmetry at the phosphorus atom of the nucleotide yields a diasymmetric nucleotide. Such a diasymmetric nucleotide is a chiral nucleotide having Sp and Rp diastereomers.

Substitution of one of the oxygen atoms of the phosphate moiety of a nucleotide with a sulfur atom yields Sp and Rp diastereomeric phosphorothioate analogs. Similarly, substitution of a phosphate oxygen atom by an alkyl moiety yields diastereomeric alkylphosphonate analogs. Substitution with an alkoxy group yields diastereomeric Sp and Rp phosphotriesters. Substitution with a thioalkoxy group yields a mixed triester—a phosphodiesterthioester. Substitution with an amine or a substituted amine (including heterocyclic amines) yields diastereomeric Sp and Rp phosphoramidates.

It will be appreciated that the terms "phosphate" and "phosphate anion" as employed in connection with the present invention include nucleotides and oligonucleotides derived by replacement of one of the oxygen atoms of a naturally occurring phosphate moiety with a heteroatom, an alkyl group or an alkyoxy group. Thus, the terms "phosphate" or "phosphate anion" include naturally occurring nucleotides, phosphodiesters of naturally occurring oligonucleotides, as well as phosphorothioate, alkylphosphonate, phosphotriester, and phosphoamidate oligonucleotides.

Since there exist numerous phosphodiester linkages in an oligonucleotide, substitution of an oxygen atom by another atom such as, for example, sulfur, nitrogen, or carbon in one or more of the phosphate moieties yields a racemic mixture unless such substitution occurs in a stereospecific manner. As a practical matter, see Stec, W. J., Zon, G., and Uznanski, B. (1985), *J. Chromatography*, 326:263, above. Separation of the diastereomers of racemic mixtures of non-stereospecific synthesized oligonucleotides is only possible when there are a minimum of diasymmetric sites, for example, two diasymmetric sites. Since the diasymmetric substituent group at each diastereomeric phosphorus atom could have steric, ionic or other effects on conformation, binding, and the like at each such site, sequence-specific oligonucleotides having all Sp or all Rp chiral phosphorus linkages are desirable.

In accordance with this invention, sequence-specific oligonucleotides are provided comprising substantially pure chiral phosphate linkages such as, for example, phosphorothioate, methylphosphonate, phosphotriester or phosphoramidate linkages. In contrast to prior art synthetic oligonucleotides, at least certain of the chiral phosphorous linkages of the present oligonucleotides are not racemic in nature but, rather, possess relatively high enantiomeric purity. As will be recognized by those skilled in the art, enantiomeric purity—also known as chiral purity—is manifested for a chemical compound by the predominance of one enantiomer over the other. Thus, an oligonucleotide can be said to possess a substantially pure chiral phosphate linkage where, for example, the Sp form of that linkage greatly predominates over the Rp form. In accordance with the present invention, at least certain of the chiral phosphate linkages present in an oligonucleotide should have chiral purity greater than about 75%. Preferably such linkages have chiral purity greater than about 90%, more preferably greater than about 95%, even more preferably about 100%. Chiral purity may be determined by any of the many methods known in the art, including but not limited to x-ray diffraction, optical rotary dispersion, and circular dichroism.

The oligonucleotides of the invention are expected to exhibit one or more efficacious properties such as, for example, hybridization with targeted RNA's and DNA's, cellular absorption and transport, or improved enzymatic interaction. At the same time, it is expected that these improvements to the basic oligonucleotide sequences will not significantly diminish existing properties of the basic oligonucleotide sequence. Thus, the present improvements are likely to lead to improved drugs, diagnostics, and research reagents.

Further improvements likely can be effected by making one or more substitutions or modifications to the base or the sugar moieties of the individual nucleosides employed to prepare the chiral oligonucleotides of the invention. Such substitutions or modifications generally comprise derivation at a site on the nucleoside base or at a site on the nucleoside sugar, provided such derivation does not interfere with the stereoselective syntheses of the present invention by, for example, blocking nucleophilic attack of the 5'-phosphate of a first synthon at the 3'-position of a second synthon. In certain embodiments, one or more of the nucleosides of the chiral oligonucleotides of the invention include a naturally occurring nucleoside unit which has been substituted or modified. These non-naturally occurring or "modified" nucleoside units preferably have either structure (4) or structure (5):

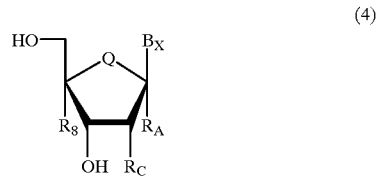

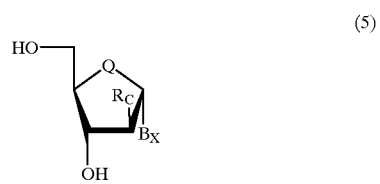

wherein:

Q is O or $CHR_G$;

$R_A$ and $R_B$ are H, lower alkyl, substituted lower alkyl, an RNA cleaving moiety, a group which improves the pharmacokinetic properties of an oligonucleotide, or a group which improves the pharmacodynamic properties of an oligonucleotide;

$R_C$ is H, OH, lower alkyl, substituted lower alkyl, F, Cl, Br, CN, $CF_3$, $OCF_3$, OCN, O-alkyl, substituted O-alkyl, S-alkyl, substituted S-alkyl, SOMe, $SO_2Me$, $ONO_2$, $NO_2$, $N_3$, $NH_2$, NH-alkyl, substituted NH-alkyl, $OCH_2CH=CH_2$, $OCH=CH_2$, $CH_2CCH$, OCCH, aralkyl, heteroaralkyl, heterocycloalkyl, polyalkylamino, substituted silyl, an RNA cleaving moiety, a group which improves the pharmacodynamic properties of an oligonucleotide, or a group which improves the pharmacokinetic properties of an oligonucleotide;

$R_G$ is H, lower alkyl, substituted lower alkyl, an RNA cleaving moiety, a group which improves the pharmacokinetic properties of an oligonucleotide, or a group which improves the pharmacodynamic properties of an oligonucleotide; and $B_X$ is a nucleoside base, a blocked nucleoside base, a nucleoside base analog, or a blocked nucleoside base analog.

In preferred embodiments $B_X$ is a pyrimidinyl-1 or purinyl-9 moiety as for instance adenine, guanine, hypoxanthine, uracil, thymine, cytosine, 2-aminoadenine or 5-methylcytosine. Preferably, $B_X$ is selected such that a modified nucleoside has one of the structures (6)–(11):

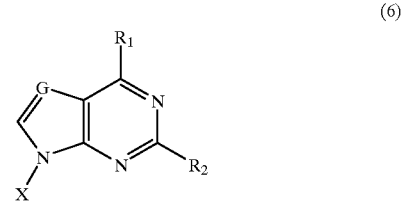

-continued

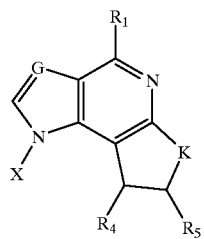
(7)

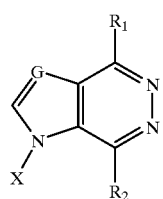
(8)

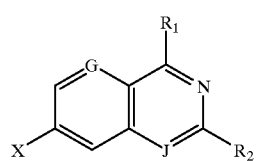
(9)

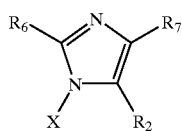
(10)

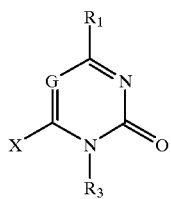
(11)

wherein:

G and K are, independently, C or N;

J is N or $CR_2R_2$;

$R_1$ is OH or $NH_2$;

$R_2$ and $R_3$ are H, NH, lower alkyl, substituted lower alkyl, lower alkenyl, aralkyl, alkylamino, aralkylamino, substituted alkylamino, heterocycloalkyl, heterocycloalkylamino, aminoalkylamino, hetrocycloalkylamino, polyalkylamino, an RNA cleaving moiety, a group which improves the pharmacokinetic properties of an oligonucleotide, or a group which improves the pharmacodynamic properties of an oligonucleotide;

$R_4$ and $R_5$ are, independently, H, OH, $NH_2$, lower alkyl, substituted lower alkyl, substituted amino, an RNA cleaving moiety, a group which improves the pharmacokinetic properties of an oligonucleotide, or a group which improves the pharmacodynamic properties of an oligonucleotide;

$R_6$ and $R_7$ are, independently, H, OH, $NH_2$, SH, halogen, $CONH_2$, $C(NH)NH_2$, $C(O)O$-alkyl, $CSNH_2$, CN, $C(NH)NHOH$, lower alkyl, substituted lower alkyl, substituted amino, an RNA cleaving moiety, a group which improves the pharmacokinetic properties of an oligonucleotide, or a group which improves the pharmacodynamic properties of an oligonucleotide; and X is a sugar or a sugar analog moiety where said sugar analog moiety is a sugar substituted with at least one substituent comprising an RNA cleaving moiety, a group which improves the pharmacodynamic properties of an oligonucleotide, or a group which improves the pharmacokinetic properties of an oligonucleotide. It is preferred that X have the general structure (4) or (5).

For the purposes of this invention, improving pharmacodynamic properties means improving oligonucleotide uptake, enhanced oligonucleotide resistance to degradation, and/or strengthened sequence-specific hybridization with RNA and improving pharmacokinetic properties means improved oligonucleotide uptake, distribution, metabolism or excretion. RNA cleaving moieties are chemical compounds or residues which are able to cleave an RNA strand in either a random or, preferably, a sequence-specific fashion.

Exemplary base moieties of the invention are any of the natural pyrimidinyl-1- or purinyl-9- bases including uracil, thymine, cytosine, adenine, guanine, 5-alkylcytosines such as 5-methylcytosine, hypoxanthine, 2-aminoadenine, and other modified bases as depicted in the formulas above. Exemplary sugars include ribofuranosyl, 2'-deoxyribofuranosyl, their corresponding five membered ring carbocyclic analogs as well as other modified sugars depicted in the formulas above. Particularly preferred modified sugars include 2'-fluoro and 2'-O-methyl-2'-deoxyribofuranosyl, i.e. 2'-fluoro and 2'-O-methyl-β-D-erythro-pentofuranosyl.

Alkyl groups of the invention include but are not limited to $C_1$–$C_{12}$ straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl, 2-propylpentyl. Alkenyl groups include but are not limited to unsaturated moieties derived from the above alkyl groups including but not limited to vinyl, allyl, crotyl, propargyl. Aryl groups include but are not limited to phenyl, tolyl, benzyl, naphthyl, anthracyl, phenanthryl, and xylyl. Halogens include fluorine, chlorine, bromine, and iodine. Suitable heterocyclic groups include but are not limited to imidazole, tetrazole, triazole, pyrrolidine, piperidine, piperazine, and morpholine. Carbocyclic groups include 3, 4, 5, and 6-membered substituted and unsubstituted alkyl and alkenyl carbocyclic rings. Amines include amines of all of the above alkyl, alkenyl, and aryl groups including primary and secondary amines and "masked amines" such as phthalimide. Amines are also meant to include polyalkylamino compounds and aminoalkylamines such as aminopropylamine and further heterocycloalkylamines such as imidazol-1, 2 or 4-yl-propylamine. Substituent groups for the above include but are not limited to other alkyl, haloalkyl, alkenyl, alkoxy, thioalkoxy, haloalkoxy, and aryl groups as well as halogen, hydroxyl, amino, azido, carboxy, cyano, nitro, mercapto, sulfides, sulfones, and sulfoxides. Other suitable substituent groups also include rhodamines, coumarins, acridones, pyrenes, stilbenes, oxazolo-pryidocarbazoles, anthraquinones, phenanthridines, phenazines, azidobenzenes, psoralens, porphyrins, cholesterols, and other "conjugate" groups.

Methods of synthesizing such modified nucleosides are set forth in copending applications for United States Letters Patent, assigned to the assignee of this invention, and entitled Compositions and Methods for Modulating RNA Activity, Ser. No. 07/463,358, filed Jan. 11, 1990; Sugar Modified Oligonucleotides That Detect And Modulate Gene Expression, Ser. No. 07/566,977, filed Aug. 13, 1990; and Compositions and Methods for Modulating RNA Activity, U.S. Ser. No. 91/00243, filed Jan. 11, 1991, the entire disclosures of which are incorporated herein by reference.

The chirally pure phosphorothioate, methylphosphonate, phosphotriester or phosphoramidate oligonucleotides of the invention can be evaluated for their ability to act as inhibitors of RNA translation in vivo. Various therapeutic areas can be targeted for such antisense potential. These therapeutic areas include but are not limited to herpes virus (HSV), the TAR and tat regions of HIV, the codon regions of *Candida albicans* chitin synthetase and *Candida albicans* β tubulin, papilloma virus (HPV), the ras oncogene and protooncogene, ICAM-1 (intercellular adhesion molecule-1) cytokine, and 5'-lipoxygenase. A targeted region for HSV includes GTC CGC GTC CAT GTC GGC (SEQ ID NO:1). A targeted region for HIV includes GCT CCC AGG CTC AGA TCT (SEQ ID NO:2). A targeted region for *Candida albicans* includes TGT CGA TAA TAT TAC CA (SEQ ID NO:3). A targeted region for human papillomavirus, e.g. virus types HPV-11 and HPV-18, includes TTG CTT CCA TCT TCC TCG TC (SEQ ID NO:4). A targeted region for ras includes TCC GTC ATC GCT CCT CAG GG (SEQ ID NO:5). A targeted region for ICAM-1 includes TGG GAG CCA TAG CGA GGC (SEQ ID NO:6) and the sequence CGA CTA TGC AAG TAC (SEQ ID NO:7) is a useful target sequence for 5-lipoxygenase. In each of the above sequences the individual nucleotide units of the oligonucleotides are listed in a 5' to 3' sense from left to right.

The phosphorothioate, methylphosphonate, phosphotriester or phosphoramidate oligonucleotides of the invention may be used in therapeutics, as diagnostics, and for research, as specified in the following copending applications for United States Letters Patent assigned to the assignee of this invention: Compositions and Methods for Modulating RNA Activity, Ser. No. 07/463,358, filed Jan. 11, 1990; Compositions and Methods for Detecting and Modulating RNA Activity, Ser. No. 07/463,358, filed Jan. 11, 1990; Antisense Oligonucleotide Inhibitors of Papilloma Virus, Ser. No. 07/445,196 Filed Dec. 4, 1989; Oligonucleotide Therapies for Modulating the Effects of Herpesvirus, Ser. No. 07/485, 297, filed Feb. 26, 1990; Reagents and Methods for Modulating Gene Expression Through RNA Mimicry Ser. No. 07/497,090, filed Mar. 21, 1990; Oligonucleotide Modulation of Lipid Metabolism, Ser. No. 07/516,969, filed Apr. 30, 1990; Oligonucleotides for Modulating the Effects of Cytomegalovirus Infections, Ser. No. 07/568,366, filed Aug. 16, 1990; Antisense Inhibitors of the Human Immunodeficiency Virus, Ser. No. 09/521,907, filed May 11, 1990; Nuclease Resistant Pyrimidine Modified Oligonucleotides for Modulation of Gene Expression, Ser. No. 07/558,806, filed Jul. 27, 1990; Novel Polyamine Conjugated Oligonucleotides, Ser. No. 07/558,663, filed Jul. 27, 1990; Modulation of Gene Expression Through Interference with RNA Secondary Structure, Ser. No. 07/518,929, filed May 4, 1990; Oligonucleotide Modulation of Cell Adhesion, Ser. No. 07/567,286, filed Aug. 14, 1990; Inhibition of Influenza Viruses, Ser. No. 07/567,287, filed Aug. 14, 1990; Inhibition of Candida, Ser. No. 07/568,672, filed Aug. 16, 1990; and Antisense Oligonucleotide Inhibitors of Papillomavirus, Ser. No. PCT/US90/07067, filed Dec. 3, 1990. These patents disclose a number of means whereby improved modulation of RNA and DNA activity may be accomplished through oligonucleotide interaction. To the extent that the specific sequences disclosed therein may be used in conjunction with the present invention, the disclosures of the foregoing United States patent applications are incorporated herein by reference.

The oligonucleotides of the invention preferably are prepared via the process shown in Scheme 1, wherein a selected nucleotide is coupled to another nucleotide or to a growing oligonucleotide chain via a nucleophilic displacement reaction. As will be recognized, this process is also applicable to the preparation of oligonucleotides comprising non-chiral phosphodiester linkages. In Scheme 1, $R_F$ is a phosphate blocking group, $B_X$ is a suitable heterocyclic nucleoside base (blocked or unblocked), $R_X$ is a sugar derivatizing group and Q is an oxygen or methylene group. Together $R_D$ and $R_E$ are the necessary oxygen, sulfur, nitrogen, substituted nitrogen, alkoxy or thioalkoxy groups that form the phosphorothioate, methylphosphonate, phosphotriester or phosphoramidate linking groups. For Scheme 1, the Y group of the above formulas is depicted as a CPG (Controlled Pore Glass) group. Other Y groups also may be used.

SCHEME 1

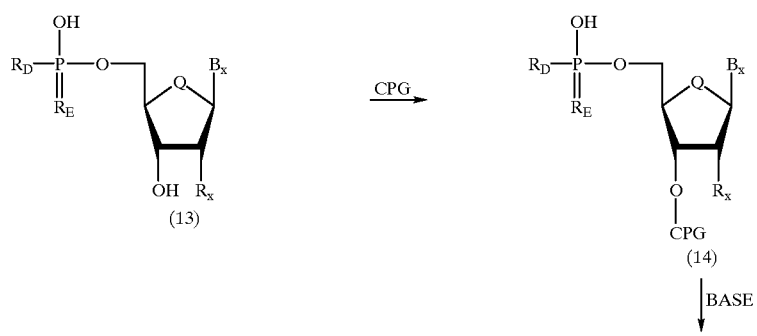

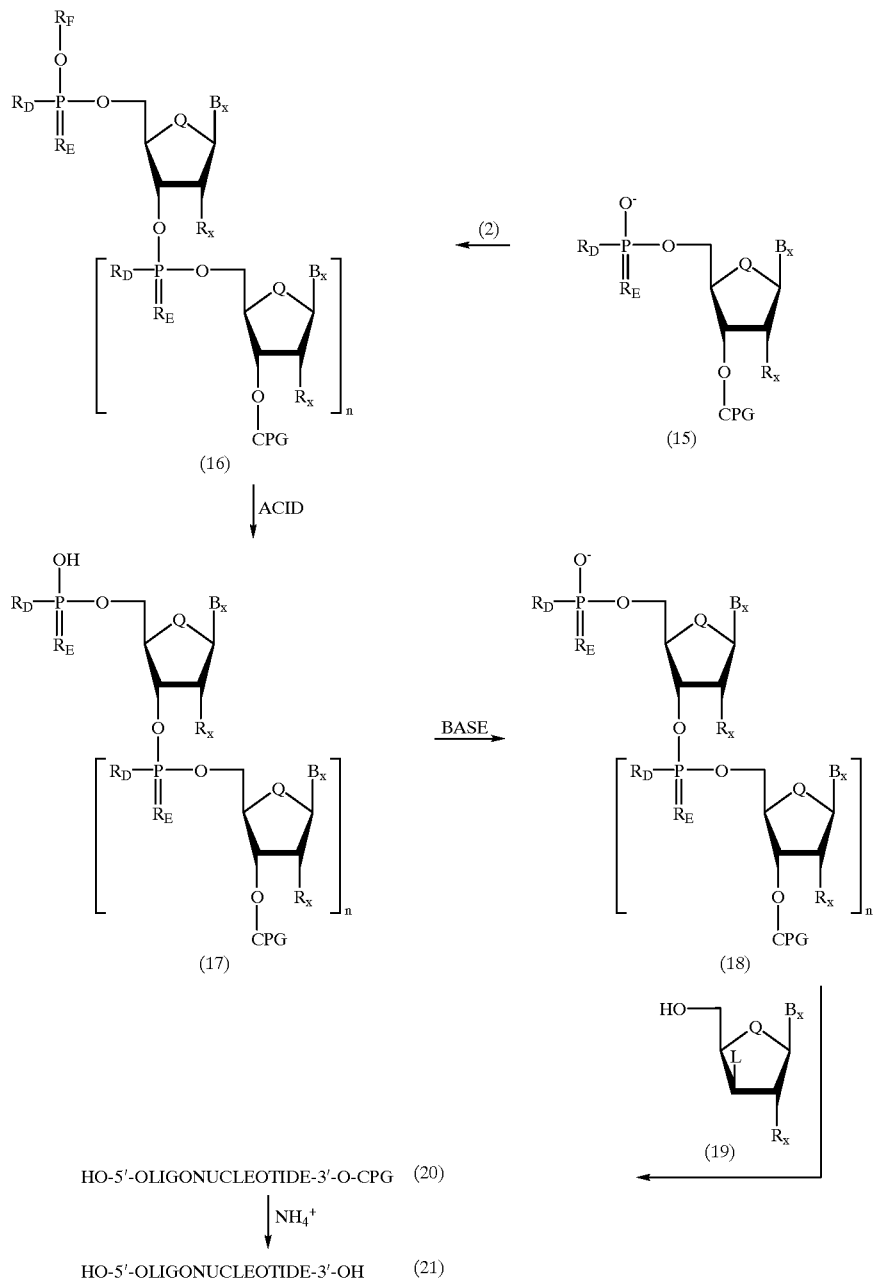

HO-5'-OLIGONUCLEOTIDE-3'-O-CPG (20)

$\downarrow NH_4^+$

HO-5'-OLIGONUCLEOTIDE-3'-OH (21)

In Scheme 1, a first nucleotide (13) is attached to a solid state CPG support via its 3'-hydroxyl group in a standard manner, yielding compound (14). Compound (14), which forms a first synthon, is treated with an appropriate base, producing anionic compound (15). Compound (15) is reacted with a first unit of compound (2)—a xylofuranosyl nucleotide bearing blocking group $R_F$ on its phosphate functionality and leaving group L at its 3' position. Compound (2) is a second synthon. The $B_X$ moiety of structure (2) may be the same as or different than the $B_X$ moiety of compound (15), depending on the sequence of the desired oligonucleotide. The anion of compound (15) displaces the leaving group at the 3' position of compound (2). The displacement proceeds via inversion at the 3' position of the second synthon, forming compound (16) with n=1.

The resulting phosphorothioate, methylphosphonate, phosphotriester or phosphoramidate linkage of compound (16) extends from the 5' position of the first synthon (compound (14)) to the 3' position of the second synthon (compound (2)). The inversion at the 3' position of the second synthon results in the final configuration at the 3' nucleotide derived from the second synthon being a normal ribofuranosyl sugar conformation. Compound (16) on the solid state CPG support is now washed to free it of any unreacted compound (2).

The second synthon carries a phosphate blocking group $R_F$ on its phosphorothioate, methylphosphonate, phosphotriester or phosphoramidate phosphorus group. After coupling of the second synthon to the first synthon to yield compound (16) wherein n=1 and washing, the phosphate blocking group $R_F$ is removed with an acid, yielding compound (17) wherein n=1. Compound (17), which represents a new first synthon, is now treated with base to generate a further anionic, compound (18) with n=1. Compound (18) is suitable for nucleophilic attack on a further unit of compound (2) (the second synthon) to form a new compound (16) wherein n=2. In this further unit having compound (2), the $B_X$ moiety may be the same or different from the $B_X$ moiety of either of the nucleotides of compound (16) wherein n=1, depending on the desired sequence.

Compound (16) wherein n=2 is washed and then treated with acid to deblock the $R_F$ blocking group, yielding a further new first synthon, compound (17) wherein n=2. This new first synthon, is now ready to be further cycled by treatment with base to yield compound (18) wherein n=2, which is now reacted with a further unit having compound (2) to yield a further unit of having structure (16) wherein n=3. Again, $B_X$ may be the same or different than previously $B_X$ moieties. The cycle is repeated for as many times as necessary to introduced further nucleotides of the desired sequence via compound (2).

If it is desired to have the 5' terminal end of the final oligonucleotide as a phosphate group, then the last compound (17) is appropriately removed from the CPG support. If it is desired to have the 5' terminal end as a hydroxyl group, then the penultimate nucleotide is added as compound (22), it is converted to compounds (16), (17), and (18) and the resulting compound (18) is reacted with a xylofuranosyl nucleoside, compound (19). Compound (19), like compound (2), includes a leaving group L within its structure. Reaction of compound (19) with compound (18) yields oligonucleotide, compound (20), which is released from the CPG support with concentrated ammonium ion to yield the desired oligonucleotide, compound (21). The ammonium ion treatment will also remove any base blocking groups as is standard in automated oligonucleotide synthesis.

In summary, as shown in Scheme 1, a phosphorothioate, methylphosphonate, phosphotriester or phosphoramidate 5' nucleotide (or the 5'-terminal nucleotide of a growing oligonucleotide) functions as a first synthon. This is converted to an anion with a base. This anion displaces a leaving group at the 3' position of a xylofuranosyl nucleotide. The xylofuranosyl nucleotide comprises a second synthon. The displacement proceeds via inversion at the 3' position of the second synthon with the resulting phosphorothioate, methylphosphonate, phosphotriester or phosphoramidate linkage that is formed extending from the 5' position of the first synthon to the 3' position of the second synthon. The inversion at the 3' position of the second synthon results in the final configuration at the 3' nucleotide derived from the second synthon being a normal ribofuranosyl sugar conformation. It has a 3' to 4' trans orientations (a ribofuranosyl sugar conformation) that is identical to natural or wild type oligonucleotides.

The second synthon carries a phosphate blocking group on its phosphorothioate, methylphosphonate, phosphotriester or phosphoramidate phosphorus group. After coupling of the second synthon to the first synthon, this phosphate blocking group is removed, generating a new first synthon having an anion at its 5' phosphate suitable for nucleophilic attack on a further second synthon. Thus, after coupling of the first and second synthon, the newly joined first and second synthons now form a new first synthon. The oligonucleotide is elongated nucleotide by nucleotide via the nucleophilic attack of a phosphate anion at the 5' end of the growing oligonucleotide chain on the leaving group at the 3' position of the soon-to-be-added xylofuranosyl configured second synthon nucleotide.

It is presently preferred that the phosphate blocking group be a base stable, acid labile group. Such a phosphate blocking group maintains the phosphate moiety of the second synthon in a protected form that cannot react with the leaving group of the second synthon. This inhibits polymerization of the second synthon during the coupling reaction.

The nucleophilic coupling of the first and second synthons is a stereoselective coupling process that maintains the stereospecific configuration about the phosphorus atom of the first synthon. Thus the particular Sp or Rp diastereomeric configuration of a resolved phosphorothioate, methylphosphonate, phosphotriester or phosphoramidate moiety at the 5' end of a starting second synthon nucleotide or the 5' terminal end of a growing first synthon oligonucleotide is maintained. While the sugar portion of the second synthon undergoes inversion about its 3' position as a result of the coupling process, the phosphate portion of the second synthon retains its stereospecific configuration. After coupling of the second synthon to the first, the phosphate moiety (for example, the phosphorothioate, alkylphosphate, phosphoamidate or phosphotriester moiety) of the second synthon retains its original stereochemistry. That is, an Rp diastereomeric second synthon retains the Rp configuration of its phosphate moiety, while an Sp diastereomeric second synthon retains the Sp configuration of its phosphate moiety.

For example, to form an Rp chiral phosphorothioate, methylphosphonate, phosphotriester or phosphoramidate oligonucleotide a first Rp diastereomeric nucleotide is chosen as the first synthon. It is coupled with an Rp diastereomeric second synthon nucleotide. The resulting dinucleotide maintains the Rp orientation at the inter-nucleotide linkage between the first and second nucleotides. When a third nucleotide is next coupled to the first two, the Rp diastereomeric phosphate moiety from the second nucleotide forms the inter-nucleotide linkage between the second and third nucleotides and is maintained in the Rp orientation. If the third nucleotide was also an Rp diastereomeric nucleotide then when a fourth nucleotide is added to the growing oligonucleotide chain, the inter-nucleotide linkage between nucleotides three and four is also an Rp diastereomeric linkage. If each added "second synthon" is also an Rp diastereomer, then the resulting oligonucleotide will contain only Rp inter-nucleotide linkages. If an oligonucleotide having Sp inter-nucleotide linkages is desired, then the first nucleotide and each of the added subsequent nucleotides are selected as Sp diastereomeric nucleotides.

The first synthon can be a first nucleotide or a growing oligonucleotide chain. If it is desired that each of the nucleotides of the oligonucleotide be ribofuranoside configured nucleotides, then the first nucleotide is selected as a ribofuranoside configured nucleotide. Each added second synthon, while added as a xylofuranoside configured nucleotide, after inversion is converted to a ribofuranoside configured nucleotide.

The 3' position of the first nucleotide is either blocked if a solution reaction is practiced or is coupled to a solid state support if a solid state reaction (as for instance one utilizing a DNA synthesizer) is practiced. Each additional nucleotide of the oligonucleotide is then derived from a xylofuranosyl nucleotide, i.e. a second synthon. Because the first nucleotide of the oligonucleotide can be a "standard" ribofuranosyl nucleotide coupled via its 3' hydroxyl to a solid state support, the standard solid state supports known in the art, such as controlled pore glass (CPG) supports, can be utilized and the second synthons added as reagents to the growing oligonucleotide on a standard DNA synthesizer such as, for example, an Applied Biosystems Inc. 380B Nucleic Acid Synthesizer. However, unlike standard DNA synthesizer techniques, nucleotide coupling is not achieved using activated phosphoamidate chemistry. Instead, the above-noted nucleophilic displacement reaction of a phosphate anion on a 3' leaving group of a xylofuranosyl nucleotide is utilized as the coupling reaction. Even when chiral phosphoramidate phosphate linkages are being incorporated into the sequence-specific chiral oligonucleotides of the invention, the phosphoramidate groups of individual nucleotides are not directly used to effect the coupling reaction between nucleotides. Rather, as with phosphorothioates, alkylphosphonates, and phosphotriesters, an anion is generated at the phosphate moiety. It is this anion—not an activated amidate species—that is the activated species for effecting coupling.

Once the first nucleotide is loaded on a solid state support utilizing standard techniques, the anion necessary for nucleophilic attack is generated via treatment of the first nucleotide, i.e. the first synthon, with a base. Suitable bases include but are not limited to sodium hydride, methylmagnesium chloride, and t-butylmagnesium chloride. These are used in a suitable solvent such as acetonitrile, tetrahydrofuran or dioxane.

The second synthon is added either concurrently with the base or subsequent to it. After coupling, the growing oligonucleotide is washed with a solvent and then treated with a reagent to effect deblocking of the phosphate blocking group of the second synthon. If a preferred acid-labile blocking group is used to block the phosphate of the second synthon, deblocking is easily effected by treating the growing oligonucleotide on the solid state support with an appropriate acid.

Suitable acid-labile blocking groups for the phosphates of the second synthon include but are not limited to t-butyl, dimethoxytrityl (DMT) or tetrahydropyranyl groups. Suitable acids for deblocking the second synthon phosphate blocking group include but are not limited to acetic acid, trichloroacetic acid, and trifluoromethane sulfonic acid. Such acids are suitably soluble in solvents such as tetrahydrofuran, acetonitrile, dioxane, and the like.

Following treatment with an appropriate deblocking reagent to effect deblocking of the phosphate protecting group, the growing oligonucleotide is then washed with an appropriate solvent such as tetrahydrofuran, acetonitrile or dioxane. The oligonucleotide is now ready for the addition of a further nucleotide via treatment with base to generate an anion on the 5' terminal phosphate followed by the addition of a further second synthon. Alternatively, the anion can be generated concurrently with addition of a further second synthon. Suitable leaving groups for inclusion at the 3' position of the xylofuranosyl second synthon include but are not limited to the group consisting of halogen, alkylsulfonyl, substituted alkylsulfonyl, arylsulfonyl, substituted arylsulfonyl, hetercyclcosulfonyl or trichloroacetimidate. A more preferred group includes chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl, and 2,4,6-trichlorophenyl. These leaving groups are subject to $SN_2$ displacement reactions with inversion about the 3' position of the sugar to provide the required 3'-4' trans ribofuranosyl configuration after inversion. The ionized oxygen atom of the phosphate moiety of the first synthon displaces these leaving groups to effect the coupling of the first synthon to the second synthon.

A further class of leaving groups include certain sugar-base cyclonucleosides. These include 2,3' or 6,3'-cyclopyrimidines and 8,3'-cyclopurine nucleosides. These nucleosides are alternately known as anhydro nucleosides. Since the sugar-heterocycle bond of such cyclonucleosides is "syn" with the heterocycle base, nucleophilic addition with inversion at this site also yields the desired ribofuranoside configuration of the added nucleotide after addition of the second synthon to the first synthon. The linking atom between the 3' position of the sugar and the 2 or 6 position of a pyrimidine base or the 3' position of the sugar and the 8 position of the purine base can be oxygen, sulfur or nitrogen.

Since a basic environment is created during coupling of the first synthon to the second synthon and an acidic environment (utilizing the preferred acid-labile phosphate blocking group) is created during deblocking of the phosphate blocking group from the nucleotide derived from the second synthon, if blocking groups are utilized on the base or sugar portions of the nucleotides such base or sugar blocking groups must be stable to both acidic and basis conditions. Suitable blocking groups for the heterocyclic base or the sugar are selected to be stable to these conditions. One type of blocking groups that can be used are acid-base stable, hydrogenolysis-sensitive blocking groups; that is, blocking groups which can be removed with molecular hydrogen but not with acid or base. A benzyl blocking group is such a suitable hydrogenolysis-sensitive blocking group.

Other heterocycle base or sugar blocking groups are those that require more pronounced acid or base treatment to de-block than may be experienced during the basic activation of the nucleophilic displacement reaction of the second synthon blocking group or the acidic removal of the phosphate blocking group. Two such blocking groups are the benzoyl and isobutyryl groups. Both of these require strong basic conditions for their removal. These basic conditions are more stringent than that required to generate the phosphate anion for the nucleophilic displacement reaction. This allows the use of such benzoyl or isobutyryl blocking groups for the 6-amino group of adenine, the 2-amino group of guanine, and the 4-amino group of cytosine. Suitable precursor molecules for the second synthons include the xylo derivatives of the common nucleosides. Certain of these "xylo nucleosides" are commercially available and others are known in the nucleoside literature.

Xylo nucleosides include but are not limited to xylo derivatives of adenosine, guanosine, inosine, uridine, cytidine, thymidine, 5-methylcytidine, and 2-aminoadenosine, i.e. 9-($\beta$-D-xylofuranosyl)adenine, 9-($\beta$-D-xylofuranosyl)guanine, 9-($\beta$-D-xylofuranosyl) hypoxanthine, 1-($\beta$-D-xylofuranosyl)uracil, 1-($\beta$-D-xylofuranosyl)cytosine, 1-($\beta$-D-xylofuranosyl)thymine, 5-methyl-1-($\beta$-D-xylofuranosyl)cytosine, and 2-amino-9-($\beta$-D-xylofuranosyl)adenine. They also include the xylo equivalents of the common 2'-deoxy nucleosides such as 9-($\beta$-D-2'-deoxy-threo-pentofuranosyl)adenine, 9-($\beta$-D-2'-deoxy-threo-pentofuranosyl)guanine, 9-($\beta$-D-2'-deoxy-threo-pentofuranosyl)hypoxanthine, 1-($\beta$-D-2'-deoxy-threo-pentofuranosyl)uracil, 1-($\beta$-D-2'-deoxy-threo-pentofuranosyl)cytosine, 1-($\beta$-D-2'-deoxy-threo-pentofuranosyl)thymine,5-methyl-1-($\beta$-D-2'-deoxy-threo-pentofuranosyl)cytosine, and 2-amino-9-($\beta$-D-2'-deoxy-threo-pentofuranosyl)adenine.

Other preferred nucleosides that are suitable precursors for the second synthon include but are not limited to 2'-fluoro, 2'-methoxy, 2'-O-allyl, 2'-methyl, 2'-ethyl, 2'-propyl, 2'-chloro, 2'-iodo, 2'-bromo, 2'-amino, 2'-azido, 2'-O-methyl, 2'-O-ethyl, 2'-O-propyl, 2'-O-nonyl, 2'-O-pentyl, 2'-O-benzyl, 2'-O-butyl, 2'-O-(propylphthalimide), 2'-S-methyl, 2'-S-ethyl, 2'-aminononyl, 2'-aralkyl, and 2'-alkylheterocyclo such as propylimidazoyl derivatives of the above 2'-deoxy-threo-pentofuranosyl nucleosides. Representatives of this group include but are not limited to 9-(β-D-2'-deoxy-2'-fluoro-threo-pentofuranosyl)adenine, 9-(β-D-2'-deoxy-2'-fluoro-threo-pentofuranosyl)guanine, 9-(β-D-2'-deoxy-2-fluoro-threo-pentofuranosyl) hypoxanthine, 1-(β-D-2'-deoxy-2'-fluoro-threo-pentofuranosyl)uracil, 1-(β-D-2'-deoxy-2'-fluoro-threo-pentofuranosyl)cytosine, 1-(β-D-2'-deoxy-2'-fluoro-threo-pentofuranosyl)thymine, 5-methyl-1-(β-D-2'-deoxy-2'-fluoro-threo-pentofuranosyl)cytosine, 2-amino-9-(β-D-2'-deoxy-2'-fluoro-threo-pentofuranosyl)adenine, 9-(β-D-2'-deoxy-2'-methoxy-threo-pentofuranosyl)adenine, 9-(β-D-2'-deoxy-2'-methoxy-threo-pentofuranosyl)guanine, 9-(β-D-2'-deoxy-2-methoxy-threo-pentofuranosyl)hypoxanthine, 1-(β-D-2'-deoxy-2'-methoxy-threo-pentofuranosyl)uracil, 1-(β-D-2'-deoxy-2'-methoxy-threo-pentofuranosyl) cytosine,1-(β-D-2'-deoxy-2'-methoxy-threo-pentofuranosyl)thymine, 5-methyl-1-(β-D-2'-deoxy-2'-methoxy-threo-pentofuranosyl)cytosine,2-amino-9-(β-D-2'-deoxy-2'-methoxy-threo-pentofuranosyl)adenine, 9-(β-D-2'-deoxy-2'-O-allyl-threo-pentofuranosyl)adenine, 9-(β-D-2'-deoxy-2'-O-allyl-threo-pentofuranosyl)guanine, 9-(β-D-2'-deoxy-2'-O-allyl-threo-pentofuranosyl)hypoxanthine, 1-(β-D-2'-deoxy-2'-O-allyl-threo-pentofuranosyl)uracil, 1-(β-D-2'-deoxy-2'-O-allyl-threo-pentofuranosyl)cytosine, 1-(β-D-2'-deoxy-2'-O-allyl-threo-pentofuranosyl)thymine, 5-methyl-1-(β-D-2'-deoxy-2-O-allyl-threo-pentofuranosyl) cytosine,2-amino -9-(β-D-2'-deoxy-2'-O-allyl-threo-pentofuranosyl)adenine, 9-(β-D-2'-deoxy-2'-methyl-threo-pentofuranosyl)adenine, 9-(β-D-2'-deoxy-2'-chloro-threo-pentofuranosyl)guanine, 9-(β-D-2'-deoxy-2-amino-threo-pentofuranosyl)hypoxanthine, 1-(β-D-2'-deoxy-2'-O-nonyl-threo-pentofuranosyl)uracil, 1-(β-D-2'-deoxy-2'-O-benzyl-threo-pentofuranosyl)cytosine, 1-(β-D-2'-deoxy-2'-bromo-threo-pentofuranosyl)thymine,5-methyl-1-(β-D-2'-deoxy-2'-O-butyl-threo-pentofuranosyl)cytosine, and 2-amino-9-[β-D-2'-deoxy-2'-O-(propylphthalimide)-threo-pentofuranosyl)adenine. The 2'-deoxy-2'-fluoro-threo-pentofuranosyl, and 2'-deoxy-2'-methoxy-threo-pentofuranosyl nucleosides are particularly preferred in that the 2'-fluoro and 2'-methoxy groups give improved nuclease resistance to oligonucleotide bearing these substituents on their respective nucleotides.

Further preferred nucleosides that are suitable precursors for the second synthon include but are not limited to thexylofuranosyl or 2'-deoxy-threo-pentofuranosyl derivatives of 3-deaza purine and 2-substituted amino purine nucleosides including but not limited to 3-deaza-2'-deoxyguanosine, 3-deaza-3-nonyl-2'-deoxyguanosine, 3-deaza-3-allyl-2'-deoxyguanosine, 3-deaza-3-benzyl-2'-deoxyguanosine, 3-deaza-3-nonyl-2'-deoxyguanosine, N2-[imidazol-1-yl-(propyl)]-2'-deoxyguanosine, and 2-amino-N2-[imidazol-1-yl(propyl)]adenosine.

Another preferred group of nucleoside precursors for the second synthon include the carbocyclic nucleosides, i.e. nucleosides having a methylene group in place of the pentofuranosyl ring oxygen atom. Such carbocyclic compounds may exhibit increased stability towards chemical manipulation during activation of the xylo nucleosides for nucleophilic attack.

The xylo nucleoside or derivatized xylo nucleoside is reacted with a suitable phosphorylating agent to phosphorylate the second synthon precursor. Various phosphorylation reactions are known in the art such as those described in *Nucleotide Analogs,* by Karl Heinz Scheit, John Wiley & Sons, 1980, Chapter Four—Nucleotides with Modified Phosphate Groups and Chapter Six—Methods of Phosphorylation; Conjugates Of Oligonucleotides and Modified Oligonucleotides: A Review Of Their Synthesis and Properties, Goodchild, J. (1990), *Bioconjugate Chemistry,* 1:165; and Antisense Oligonucleotides: A New Therapeutic Principle, Uhlmann, E. and Peyman, A. (1990), *Chemical Reviews,* 90:543.

Preferred phosphorylating agents include phosphoryl chlorides. Suitable phosphoryl chlorides include but are not limited to thiophosphoryl chloride, t-butoxyphosphoryl chloride, t-butoxy(methyl)phosphoryl chloride, t-butoxy-(methyl)thiophosphoryl chloride, t-butoxy(methoxy) phosphoryl chloride. Other phosphoryl chlorides may include t-butoxy(N-morpholino)phosphoryl chloride, t-butoxy(ethoxy-ethylamino)phosphoryl chloride, t-butoxy (methy-thioxy)phosphoryl chloride, and the like. Such phosphorylating agents are utilized to yield the corresponding phosphorothioate, phosphoramidate, phosphotriester, alkylphosphonates, and phosphodiester xylo nucleotides.

Even enzymatic phosphorylation is possible, as for example the phosphorylation of 9-(β-D-xylofuranosyl) guanine by nucleoside phosphotransferase from *Pseudomonas trifolii* as per the procedure of Suzaki, S., Yamazaki, A. Kamimura, A., Mitsugi, K., and Kumashior, I. (1970), *Chem. Pharm. Bull.* (*Tokyo*), 18:172.

1-(β-D-Xylofuranosyl)uracil 5'-phosphate was identified but not separated from its 3' isomer as reported by Holy, A. and Sorm, F. (1969), *Coll. Czech. Chem. Commun.,* 34:1929. Also, 9-(2'-O-benzyl-β-D-xylofuranosyl)adenine 5'-phosphate was obtained as an intermediate by Hubert-Habart, M. and Goodman, L. (1969), *Chem. Commun.,* 740. Removable of the benzyl blocking group would give the desired unblocked nucleotide.

Additionally, the alkylphosphonates can be prepared by the method of Holy, A. (1967), *Coll. Czech. Chem. Commun.,* 32:3713. Phosphorothioates have also been prepared by treatment of the corresponding nucleoside with trisimidazolyl-1-phosphinesulfide followed by acid hydrolysis with aqueous acetic acid, Eckstein, F. (1966 & 1970), *J. Am. Chem. Soc.,* 88:4292 & 92:4718, respectively. A more preferred method is by selective thiophosphorylation by thiophosphorylchloride in triethylphosphate, Murray, A. W. and Atkinson, M. R. (1968), *Biochemistry,* 7:4023.

The appropriate phosphorylated xylo nucleotide is then activated for nucleophilic displacement at its 3' position by reacting the 3'-hydroxyl group of the xylo compound with an appropriate anhydride, chloride, bromide, acyloxonium ion, or through an anhydro or cyclo nucleoside or the like to convert the 3'-hydroxyl group of the xylo nucleoside to an appropriate leaving group.

In a further method of synthesis, treatment of 2',3'-anhydroadenosine with sodium ethylmercaptide gives 9-[3-deoxy-3-(ethylthio)-β-D-xylofuranosyl]adenine. Treatment of this compound with a first synthon nucleophile may generate a terminal 2-ethylthio arabinofuranosyl nucleoside that could be desulfurized to yield the corresponding 2'-deoxynucleoside.

If during phosphorylation or conversion of the xylo 3'-hydroxyl to a 3'-activated leaving group stereospecific diastereomers are not obtained, after completion of the phosphorylation or conversion of the 3'-hydroxyl to an activated leaving group, the Rp and Sp diastereomers of these compounds will then be isolated by HPLC. This will yield pure diastereomers in a stereospecific form ready for use as the second synthons of Scheme 1.

Additional objects, advantages, and novel features of this invention will become apparent to those skilled in the art upon examination of the following examples thereof, which are not intended to be limiting.

EXAMPLE 1

Xyloadenosine

Method A—Condensation Reaction

Adenine is condensed with 1,2,3,5-tetra-O-acetyl-D-xylopentofuranoside in the presence of $TiCl_4$ as the condensation catalyst in a polar solvent utilizing the method of Szarek, W. A., Ritchie, R. G. S., and Vyas, D. M. (1978), *Carbohydr. Res.*, 62:89.

Method B—Alkylation Reaction

8-Mercaptoadenine is alkylated with 5-deoxy-5-iodo-1,2-O-isopropylidine-xylofuranose followed by treatment with acetic acid/acetic anhydride/sulfuric acid and then ammonia. This yields an 8-5'-anhydro intermediate nucleoside that is oxidized with aqueous N-bromosuccinimide to give the sulfoxide. This is blocked with benzoic anhydride and after a Pummerer rearrangement can be desulfurized with Rainey nickel to give 9-β-D-xylofuranosyladenine as per the procedure of Mizuno, Y., Knaeko, C., Oikawa, Y., Ikeda, T, and Itoh, T. (1972), *J. Am. Chem. Soc.*, 94:4737.

EXAMPLE 2

3-Deaza-9-(β-D-xylofuranosyl)guanine

In a manner similar to Example 1, Method A, 3-deazaguanine is condensed with 1,2,3,5-tetra-O-acetyl-D-xylopentofuranoside to yield the title compound.

EXAMPLE 3

$N^6$-Benzoyl-9-(2'-Deoxy-2'-fluoro-threo-pentofuranosyl) adenine

In a manner similar to Example 1, Method A, $N^5$-benzoyladenine is condensed with 1,3,5-tri-O-acetyl-2-deoxy-2-fluoro-D-threo-pentofuranoside to yield the title compound.

EXAMPLE 4

1-(2'-Deoxy-2'-methoxy-β-D-xylofuranosyl)uridine

In a manner similar to Example 1, Method A, uracil is condensed with 1,3,5-tri-O-acetyl-2-deoxy-2-methoxy-D-threo-pentofuranoside to yield the title compound.

EXAMPLE 5

1-(2'-Deoxy-2'-O-allyl-β-D-threo-pentofuranosyl)cytosine

In a manner similar to Example 1, Method A, cytosine is condensed with 1,3,5-tri-O-acetyl-2-deoxy-2-O-allyl-D-threo-pentofuranoside to yield the title compound.

EXAMPLE 6

Xyloguanosine

Method A

In a manner similar to Example 1, Method A, guanine is condensed with 1,2,3,5-tetra-O-acetyl-D-xylopentofuranoside to yield the title compound.

Method B

The chloromercury derivative of 2-acetamido-6-chloropurine is condensed with 2,3,5-tri-O-acetyl-β-D-ribofuranosylpurine utilizing the method of Lee et. al. (1971), *J. Med. Chem.*, 14:819. The condensation product was treated with ammonia to yield 2-amino-6-chloro-9-(β-D-xylofuranosyl)purine. Further treatment with sodium hydroxyethylmercaptide gives the title compound.

EXAMPLE 7

2-Amino-6-mercapto-9-(β-D-xylofuranosyl)purine

2-Amino-6-chloro-9-(β-D-xylofuranosyl)purine as prepared by the Example 6, Method B, is treated with sodium hydrosulfide to give the title compound.

EXAMPLE 8

9-(2'-Deoxy-2'-methyl-β-D-threo-pentofuranosyl)guanine

In a manner similar to Example 1, Method A, guanine is condensed with 1,3,5-tri-O-acetyl-2-deoxy-2-methyl-D-threo-pentofuranoside to yield the title compound.

EXAMPLE 9

2-Amino-xyloadenosine 2-amino-8-mercaptoadenine is treated in the manner as per Example 6, Method B to yield the title compound.

EXAMPLE 10

Carbocyclic Xyloadenosine

5-Amino-4,6-dichloropyrimidine is treated with (±)-4α-amino-2α,3β-dihydroxy-1α-cyclopentanemethanol to give a pyrimidine intermediate that is aminated and ring closed to yield the carbocyclic analog of xylofuranosyladenine as per the procedure of Vince, R. and Daluge, S. (1972), *J. Med. Chem.*, 15:171.

EXAMPLE 11

Carbocyclic Xyloinosine

5-Amino-6-chloro-pyrimidyl-4-one when treated with (±)-4α-amino-2α,3β-dihydroxy-1α-cyclopentanemethanol will give a pyrimidine intermediate that is then aminated and ring closed to yield the carbocyclic analog of xylofuranosylinosine as per the procedure of Example 8.

EXAMPLE 12

$O^2$,3'-Cyclothymidine

Method A

3'-O-Mesylthymidine is treated with boiling water and the pH is adjusted to pH 4-5 according to the procedure of Miller, N. and Fox, J. J. (1964), *J. Org. Chem.*, 29:1771 to yield the title compound. This same compound can also prepared from 3'-deoxy-3'-iodothymidine by treatment with silver acetate in acetonitrile.

Method B $O^2$,3'-Cyclothymidine and other 2'-deoxynucleosides are prepared by the treatment of the appropriate nucleoside with (2-chloro-1,1,3-trifluoroethyl)diethylamine in dimethylformamide according to the procedure of Kowollik, G., Gaertner, K., and Langen, P. (1969), *Tetrahedron Lett.*, 3863.

EXAMPLE 13

$O^2$,3'-Cyclouridine

3'-O-tosyluridine is treated with t-butoxide according to the procedure of Letters, R. and Michelson, A. M. (1961), *J. Chem. Soc.*, 1410. This compound is also prepared by treatment of 3'-O-mesyl-2',5'-di-O-trityluridine with sodium benzoate in dimethylformamide followed by detritlation with hydrochloric in chloroform.

EXAMPLE 14

$S^2$, 3'-Cyclo-2-thiothymidine

Method A

3'-O-mesyl-$O^2$,5'-cyclothymidine is subjected to methanolysis followed by sulfhydryl ion attack. The $S^2$,3'-cyclo linkage is then opened up with base to yield 2',3'-dideoxy-3'-mercapto-1-(β-D-xylofuranosyl)thymidine as per the procedure of Wempen, I. and Fox, J. J. (1969), *J. Org. Chem.*, 34:1020.

Method B

S²,3'-Cyclo-2-thiouridine is also prepared from 2-thiouridine by the method of Doerr, I. L. and Fox, J. J. (1967), *J. Am. Chem.*, 89:1760.

EXAMPLE 15

N⁶,5'-Cyclothymidine

5'-O-Trityl-3'-O-mesylthymidine is treated with sodium azide to yield N⁶,5'-cyclothymidine as one of the products. 5'-O-trityl-3'-O-mesylthymidine is also cyclizable to O²,3'-cyclothymidine.

EXAMPLE 16

8,3'-Cycloadenosine

The anhydro ring from the 3' position of the sugar to the 8 position of the purine ring is formed by treatment of 5'-O-acetyl-8-bromo-2' (or 3')-O-p-toluenesulfonyladenosine with thiourea to yield the 8,3'-thiocyclonucleoside (as well as the corresponding 8,2') product as per the procedure of Ikehara, M. and Kaneko, M. (1970), *Tetrahedron*, 26:4251.

EXAMPLE 17

8,3'-Cycloguanosine

The title compound is prepared as per Example 16 utilizing 8-bromoguanosine. Both this compound and the compound of Example 16 can be oxidized to their corresponding sulfoxides via tert-butyl hypochlorite in methanol or treated with chlorine in methanolic hydrogen chloride to yield the 3'-sulfo-8-chloro analog in a procedure analogous with that of Mizuno, Y., Kaneko, O., and Oikawa, Y. (1974), *J. Org. Chem.*, 39:1440.

EXAMPLE 18

1-(3'-Bromo-3'-deoxy-N⁴,2',5'-O-triacetylxylofuranosyl) cytosine

The title compound is prepared by treating N⁴-acetylcytidine with acetyl bromide according to the procedure of Marumoto, R. and Honjo, M. (1974), *Chem. Pharm. Bull.*, 22:128.

EXAMPLE 19

9-(3-Deoxy-3-fluoro-β-D-xylofuranosyl)adenine

Treatment of 9-(2,3-anhydro-5-O-benzoyl-β-D-ribofuranosyl)-N,N-dibenzoyl (or N-pivaloyl)adenine with tetraethylammonium fluoride in hot acetonitrile followed by deacylation with sodium methoxide yields 9-(3-deoxy-3-fluoro-β-D-xylofuranosyl)adenine as per the procedure of Lichtenthaler, F. W., Emig, P., and Bommer, D. (1969), *Chem. Ber.*, 102:964.

EXAMPLE 20

9-(3-Deoxy-3-fluoro-β-D-xylofuranosyl)guanine

In a like manner to Example 18 the corresponding guanosine compound will be prepared from the corresponding 2,3-anhydro guanosine.

EXAMPLE 21

9-(3'-Chloro-3'-deoxy-β-D-xylofuranosyl)hypoxanthine

5'-O-Acetylinosine is treated with triphenylphosphine and carbon tetrachloride to yield the title compound according to the procedure of Haga, K., Yoshikawa, M., and Kato, T. (1970), *Bull. Chem. Soc. Jpn.*, 43:3992.

EXAMPLE 22

9-(2-O-Acetyl-3-chloro-3-deoxy-5-O-pivaloyl-β-D-xylofuranosyl)-6-pivalamidopurine The title compound is prepared via an intermediate 2',3'-O-acyloxonium ion utilized to introduce a halogen atom at the 3' position and convert the ribo configuration of a nucleoside into the corresponding 3'-halo-3'-deoxy xylo nucleoside. The acyloxonium ion is generated in situ by treatment of 2',3'-O-methoxyethylidineadenosine with pivaloyl chloride in hot pyridine. Attack by chloride gives the title compound. Hypoxanthine and guanine nucleoside react in a similar manner. Sodium iodide will be used to generate the corresponding 3'-iodides according to the procedure of Robins, M. J., Fouron, Y., and Mengel, R. (1974), *J. Org. Chem.*, 39:1564.

EXAMPLE 23

9-(2,5,-Di-O-acetyl-3-bromo-3-deoxy-β-D-xylofuranosyl) adenine

This compound is prepared by a in situ acyloxonium ion generated by treating 3',5'-di-O-acetyladenosine with boron trifluoride etherate followed by phosphorus tribromide according to the procedure of Kondo, K., Adachi, T., and Inoue, I. (1977), *J. Org. Chem.*, 42:3967. The title compound can also be formed by treating adenosine with tetraacetoxysilane and phosphorus tribromide in the presence of boron trifluoride etherate.

EXAMPLE 24

1-(β-D-2'-Deoxy-2'-fluoro-threo-pentofuranosyl)uracil

In a manner similar to Example 3, uracil is condensed with 1,3,5,-tri-O-acetyl-2-deoxy-2-fluoro-D-threo-pentofuranoside to yield the title compound.

EXAMPLE 25

1-(β-D-2'-Deoxy-2'-fluoro-threo-pentofuranosyl) guanine

In a manner similar to Example 3, guanine is condensed with 1,3,5,-tri-O-acetyl-2-deoxy-2-fluoro-D-threo-pentofuranoside to yield the title compound.

EXAMPLE 26

1-(β-D-2'-Deoxy-2'-fluoro-threo-pentofuranosyl)cytosine

In a manner similar to Example 3, cytosine is condensed with 1,3,5,-tri-O-acetyl-2-deoxy-2-fluoro-D-threo-pentofuranoside to yield the title compound.

EXAMPLE 27

O²,3'-Cyclo-2'-deoxycytidine

The title compound is prepared by heating the 3'-O-sulfamate as per the procedure of Schuman, D., Robins, M. J., and Robins, R. K. (1970), *J. Am. Chem. Soc.*, 92:3434.

EXAMPLE 28

Sp and Rp Xyloadenosine 5'-Monophosphate

N⁶-Benzoyl-xyloadenosine is phosphorylated with phosphoryl chloride in pyridine and acetonitrile at 0° C. The reaction will be quenched with ice water, rendered basic and added to an activated charcoal column. After elution with ethanol/water/concentrated ammonium hydroxide the solvent is evaporated to dryness and the residue dissolved in water and passed through an ion exchange column. The benzoyl blocking group is removed in concentrated ammonium hydroxide followed by separation of the diastereomers by HPLC to yield the title compound.

EXAMPLE 29

Sp and Rp 1-(β-D-2'-Deoxy-2'-fluoro-threo-pentofuranosyl) uracil 5'-t-butoxy(methyl)phosphonate 1-(β-D-2'-deoxy-2'-fluoro-threo-pentofuranosyl)thymine will be phosphorylated with t-butoxy(methyl)phosphoryl chloride in trimethylphosphate at 0° C. for 3 hrs. The solution is added to cold anhydrous ether. The racemic precipitate is taken up in acetonitrile and the Sp and Rp diastereomers of the title compound separated by HPLC utilizing a gradient of acetonitrile and triethylammonium acetate buffer.

EXAMPLE 30

Sp and Rp 1-(β-D-2'-Deoxy-2'-fluoro-threo-pentofuranosyl) cytosine 5'-t-butoxy(methyl)phosphonate 1-(β-D-2'-deoxy-2'-fluoro-threo-pentofuranosyl)cytosine will be phosphorylated and purified as per the procedure of Example 29 to give the diastereomers of the title compound.

EXAMPLE 31

Sp and Rp $N^5$-Benzoyl-9-(β-D-2'-Deoxy-2'-fluoro-threo-pentofuranosyl)adenine 5,-t-butoxy(methyl)phosphonate $N^6$-Benzoyl-9-(β-D-2'-deoxy-2'-fluoro-threo-pentofuranosyl)adenine will be phosphorylated and purified as per the procedure of Example 29 to give the diastereomers of the title compound.

EXAMPLE 32

Sp and Rp 9-(β-D-2'-Deoxy-2'-fluoro-threo-pentofuranosyl) guanine 5'-t-butoxy(methyl)phosphonate 9-(β-D-2'-Deoxy-2'-fluoro-threo-pentofuranosyl)guanine will be phosphorylated and purified as per the procedure of Example 29 to give the diastereomers of the title compound.

EXAMPLE 33

Sp and Rp Xylofuranosyluracil 5'-t-butoxyphosphbrothioate

Xylofuranosyluracil will be phosphorothioated with t-butoxythiophosphorylchloride in triethylphosphate utilizing the method of Murray, A. W. and Atkinson, M. R. (1968), *Biochemistry*, 7:4023. The diastereomers of the title compound are separated by HPLC.

EXAMPLE 34

Sp and Rp 9-(2'-Deoxy-2'-methyl-β-D-threo-pentofuranosyl)guanine 5'-Methylphosphonate 9-(2'-Deoxy-2'-methyl-β-D-threo-pentofuranosyl) guanine will be alkylphosphonated utilizing the procedure of Holy, A. (1967), *Coll. Czech. Chem. Commun.*, 32:3713. The racemic phosphorylation product is separated into its Sp and Rp diastereomers using HPLC chromatography to yield the title compound.

EXAMPLE 35

Sp and Rp 9-(2'-Deoxy-β-D-threo-pentofuranosyl) hypoxanthine 5'-Phosphormorpholidate 9-(2'-Deoxy-β-D-threo-pentofuranosyl)hypoxanthine is phosphorylated according to the procedure of Example 28. The resulting 5'-phosphate intermediate will be phosphormorpholidated by treatment with activated with dicyclohexylcarbodiimide in the presence of morpholine according to the procedure of Moffatt, J. G. and Khorana, H. G. (1961), *J. Am. Chem. Soc.*, 83:3752 to yield the racemic title compound. The diastereomers of the product are separated by HPLC.

EXAMPLE 36

Sp and Rp 9-(2'-Deoxy-2'-O-allyl-β-D-threo-pentofuranosyl)cytosine 5'-Phosphate 9-(2'-Deoxy-2'-allyl-β-D-threo-pentofuranosyl)cytosine will be phosphorylated according to the procedure of Example 28 to yield the racemic title compound. The diastereomers are separated by HPLC.

EXAMPLE 37

Sp and Rp 9-(2'-Deoxy-2'-methoxy-β-D-threo-pentofuranosyl)-uracil 5'-Phosphate 9-(2'-Deoxy-2'-methoxy-β-D-threo-pentofuranosyl)uracil will be phosphorylated according to the procedure of Example 28 to yield the racemic title compound. The diastereomers are separated by HPLC.

EXAMPLE 38

Sp and Rp 3-Deaza-9-(xylofuranosyl)guanine 5'-Phosphate

3-Deaza-9-(xylofuranosyl)guanine will be phosphorylated according to the procedure of Example 28 to yield the racemic title compound. The diastereomers are separated by HPLC.

EXAMPLE 39

Sp and Rp Xyloguanosine 5'-Phosphorothioate

Xyloguanosine will be phosphorothioated with thiophosphoryl chloride according to the procedure of Example 28 to yield the racemic title compound. The diastereomers are separated by HPLC.

EXAMPLE 40

Sp and Rp Carbocyclic Xyloadenosine 5'-Phosphate

In a like manner to Example 28, carbocyclic xyloadenosine will be treated with phosphoryl chloride to yield the racemic title compound. The diastereomers will be separated by HPLC.

EXAMPLE 41

Activated 3'-Deoxy-3'-Active Leaving Group Phosphorylated Nucleosides

The 3'-halo nucleotides can be treated with methoxide to give an unstable 2',3'-anhydro intermediate that slowly forms the corresponding 3,3'-cyclonucleoside. The cyclonucleoside in turn can undergo nucleophilic attack to yield other 3'-deoxy-3'-substituted derivatives, as for instance, the tosyl, triflate, trichloroacetimidate or other active species.

EXAMPLE 42

$N^6$-Benzoyl-9-(3'-Deoxy-3'-tosyl-2'-deoxy-2'-fluoro-β-D-threo-pentofuranosyl)adenine 5'-Rp t-Butoxy(methyl) phosphonate $N^6$-Benzoyl-9-(2'-deoxy-2'-fluoro-β-D-threo-pentofuranosyl)adenine 5'-Rp t-butoxy(methyl)phosphonate will be treated with p-toluenesulfonlychloride in pyridine as per the procedure of Reist, E. J., Bartuska, V. J., Calkins, D. F., and Goodman, L. (1965), *J. Org. Chem.*, 30:3401 to yield the title compound.

EXAMPLE 43

9-(3'-Deoxy-3'-tosyl-2'-deoxy-2'-methoxy-β-D-threo-pentofuranosyl)uracil 5'-Rp t-Butoxy(methyl)phosphonate 9-(2'-Deoxy-2'-methoxy-β-D-threo-pentofuranosyl) uridine 5'-Rp t-butoxy(methyl)phosphonate will be treated with p-toluenesulfonlychloride in pyridine according to the procedure of Example 42 to yield the title compound.

EXAMPLE 44
9-(3'-Deoxy-3'-tosyl-2'-deoxy-2'-fluoro-β-D-threo-pentofuranosyl)uracil 5'-Rp t-Butoxy(methyl)phosphonate 9-(2'-Deoxy-2'-fluoro-β-D-threo-pentofuranosyl)uridine 5'-Rp t-butoxy(methyl)phosphonate will be treated with p-toluenesulfonlychloride in pyridine according to the procedure of Example 42 to yield the title compound.

EXAMPLE 45
9-(3'-Deoxy-3'-tosyl-2'-deoxy-2'-fluoro-β-D-threo-pentofuranosyl)cytosine 5'-Rp t-Butoxy(methyl)phosphonate 9-(2'-Deoxy-2'-fluoro-β-D-threo-pentofuranosyl)cytosine 5'-Rp t-butoxy(methyl)phosphonate will be treated with p-toluenesulfonlychloride in pyridine according to the procedure of Example 42 to yield the title compound.

EXAMPLE 46
9-(3'-Deoxy-3'-tosyl-2'-deoxy-2'-fluoro-β-D-threo-pentofuranosyl)guanine 5'-Sp Phosphate 9-(2'-Deoxy-2'-fluoro-β-D-threo-pentofuranosyl)guanine 5'-Sp phosphate will be treated with p-toluenesulfonly chloride in pyridine according to the procedure of Example 42 to yield the title compound.

EXAMPLE 47
9-(3'-Deoxy-3'-tosyl-2'-deoxy-2'-O-allyl-β-D-threo-pentofuranosyl)thymine 5'-Rp Phosphate 9-(2'-deoxy-2'-O-allyl-β-D-threo-pentofuranosyl) thymine 5'-Rp phosphate will be treated with p-toluenesulfonyl chloride in pyridine according to the procedure of Example 42 to yield the title compound.

EXAMPLE 48
3'-Deoxy-3'-trifluoromethanesulfonylxyloguanosine 5'-Sp Phosphorothioate Xyloguanosine 5'-Sp phosphorothioate will be treated with trifluoromethane sulfonic acid anhydride in the presence of a sodium hydride to yield the title compound.

EXAMPLE 49
Carbocyclic3'-Deoxy-3'-trifluoromethanesulfonylxyloadenosine 5'-Rp Phosphate In a like manner to Example 48, carbocyclic xyloadenosine 5'-Rp phosphate will be treated with trifluoromethane sulfonic acid to yield the title compound.

EXAMPLE 50
S²,3'-Cyclo-2-thiothymidine

S²,3-Cyclo-2-thiothymidine is prepared from 3'-O-mesyl-O²,5'-cyclothymidine via methanolysis followed by sulfhydryl ion attack. The S²,3'-cyclo linkage is then opened up with base to yield 2',3'-dideoxy-3'-mercapto-1-(β-D-xylofuranosyl)thymidine, Wempen, I. and Fox, J. J. (1969), *J. Org. Chem.*, 34:1020. The 3' position will then be activated to nucleophilic attack via an active leaving group such as conversion of the mercapto to a tosyl leaving group. In a like manner S²,3'-Cyclo-2-thiouridine prepared from 2-thiouridine by the method of Doerr, I. L. and Fox, J. J. (1967), *J. Am. Chem.*, 89:1760, can be ring opened and then derivatized with an activated leaving group such as a tosylate.

EXAMPLE 51
Synthesis of 2'-Deoxy-2'-fluoro substituted CGA CTA TGC AAC TAC (SEQ ID NO:8) Rp Methylphosphonate Linked Oligonucleotide 1-(2'-Fluoro-2'-deoxy-β-D-ribofuranosyl)cytosine 5'-Rp methylphosphonate will be attached via its 3' hydroxyl to CPG beads in a standard manner as practiced in automated nucleic acid synthesis. This nucleotide forms the first synthon 1

(a) Activation of Synthon 1

The beads are washed with acetonitrile and treated with 1.1 equivalents of sodium hydride in acetonitrile to form an anion on the methylphosphonate moiety.

(b) Addition of Synthon 2 and Coupling of Synthons 1 and 2

2.0 Equivalents of N⁶-Benzoyl-9-(3'-deoxy-3'-tosyl-2'-deoxy-2'-fluoro-β-D-threo-pentofuranosyl)adenine 5'-Rp t-butoxy(methyl)phosphonate in acetonitrile is added with stirring. After completion of the nucleophilic reaction and formation of the cytosine-adenine dimer as judged by tlc, the beads are filtered and washed with acetonitrile.

(c) Removal of t-Butoxy Blocking Group

The beads are re-suspended in acetonitrile and 1.5 equivalents of trichloracetic acid is added. The reaction is stirred to remove the t-butoxy blocking group on the terminal 5'-methylphosphonate group of the adenosine nucleotide, followed by washing with acetonitrile.

(d) Cycling

The reaction is cycled to step (a), followed by addition of the next synthon 2 nucleotide at step (b), and deblocking at step (c). The reaction is further cycled for each nucleotide making up the specific sequence of the oligonucleotide. After the addition of the penultimate nucleotide its phosphate moiety is activated at step (a) and the final nucleosidic unit is added at step (b) as a xylofuranosyl nucleoside. The oligonucleotide is concurrently deblocked and removed from the CPG beads by treatment with concentrate ammonium hydroxide.

What is claimed is:

1. A composition of matter having the structure:

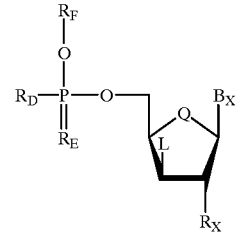

wherein:

Q is O or $CH_2$;

$R_D$ is O, S, methyl, alkoxy, thioalkoxy, amino or substituted amino;

$R_E$ is O or S;

$R_F$ is H or a blocking group;

$R_X$ is H, OH, lower alkyl, substituted lower alkyl, F, Cl, Br, CN, $CF_3$, $OCF_3$, OCN, O-alkyl, substituted O-alkyl, S-alkyl, substituted S-alkyl, SOMe, $ONO_2$, $NO_2$, $N_3$, $NH_2$, NH-alkyl, substituted NH-alkyl, $OCH_2CH\!=\!CH_2$, $OCH\!=\!CH_2$, $OCH_2CCH$, OCCH, aralkyl, heteroaralkyl, heterocycloalkyl, polyalkylamino, or substituted silyl;

$B_X$ is a nucleoside base, a blocked nucleoside base, a nucleoside base analog, or a blocked nucleoside base analog; and L is a leaving group or together L and Bx are a 2-3' or 6-3' pyrimidine or 8-3' purine cyclo-nucleoside.

2. The composition of matter of claim 1 wherein L is selected from the group consisting of halogen, alkylsulfonyl, substituted alkylsulfonyl, arylsulfonyl, substituted arylsulfonyl, hetercyclcosulfonyl or trichloroacetimidate.

3. The composition of matter of claim 1 wherein L is selected from the group consisting of chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazolesulfonyl and 2,4,6-trichlorophenyl.

4. The composition of matter of claim 1 wherein $R_F$ is selected from the group consisting of H, t-butyl, dimethoxytrityl or tetrahydropyranyl.

5. The composition of matter of claim 1 wherein $B_X$ is a pyrimidinyl-1 or purinyl-9 moiety.

6. The composition of claim 1 wherein $B_X$ is adenine, guanine, hypoxanthine, uracil, thymine, cytosine, 2-aminoadenine or 5-methylcytosine.

7. The composition of claim 1 wherein Q is O.

8. The composition of claim 1 having Sp stereochemistry.

9. The composition of claim 1 having Rp stereochemistry.

* * * * *

UNITED STATES PATENT AND TRADEMARK OFFICE
CERTIFICATE OF CORRECTION

PATENT NO.   : 6,500,945 B2
DATED        : December 31, 2002
INVENTOR(S)  : Phillip Dan Cook It is certified that error appears in the above-identified patent and that said Letters Patent is hereby corrected as shown below:

<u>Title page,</u>
Item [56], References Cited, OTHER PUBLICATIONS, "Brody" reference, please delete "bacteriphage" and insert therefor -- bacteriophage --; "Fugii" reference, please delete "Sterospecific and Steroselective" and insert therefor -- Stereospecific and Stereoselective --; and please delete "Phosphorothiates" and insert therefor -- Phosphorothioates --; and "Ikehara" reference, please delete "Nuclosides" and insert therefor -- Nucleosides --.

Signed and Sealed this

Fifteenth Day of June, 2004

JON W. DUDAS
*Acting Director of the United States Patent and Trademark Office*